United States Patent
Lau et al.

(10) Patent No.: US 7,282,024 B2
(45) Date of Patent: Oct. 16, 2007

(54) CARDIAC HARNESS HAVING INTERCONNECTED STRANDS

(75) Inventors: Lilip Lau, Los Altos, CA (US); Matthew Fishler, Sunnyvale, CA (US); Craig Mar, Fremont, CA (US); Steven Meyer, Oakland, CA (US); Anuja Patel, Sunnyvale, CA (US)

(73) Assignee: Paracor Medical, Inc., Sunnyvale, CA (US)

( * ) Notice: Subject to any disclaimer, the term of this patent is extended or adjusted under 35 U.S.C. 154(b) by 367 days.

(21) Appl. No.: 11/033,409

(22) Filed: Jan. 10, 2005

(65) Prior Publication Data

US 2005/0154253 A1  Jul. 14, 2005

Related U.S. Application Data

(60) Provisional application No. 60/535,888, filed on Jan. 12, 2004.

(51) Int. Cl.
*A61F 2/00* (2006.01)
(52) U.S. Cl. ............................. 600/37; 600/16; 623/3.1
(58) Field of Classification Search .................. 600/37, 600/16; 623/3.1, 3.16, 3.17
See application file for complete search history.

(56) References Cited

U.S. PATENT DOCUMENTS

| | | | |
|---|---|---|---|
| 2,278,926 A | 4/1942 | Hartwell | |
| 2,826,193 A | 3/1958 | Vineberg | |
| 3,464,322 A | 9/1969 | Pequignot | |
| 3,513,836 A | 5/1970 | Sausse | |
| 3,587,567 A | 6/1971 | Schiff | |
| 3,613,672 A | 10/1971 | Schiff | |
| 3,966,401 A | 6/1976 | Hancock et al. | |
| 3,983,863 A | 10/1976 | Janke et al. | |
| 3,988,782 A | 11/1976 | Dardik et al. | |
| 4,011,947 A | 3/1977 | Sawyer | |
| 4,048,990 A | 9/1977 | Goetz | |
| 4,065,816 A | 1/1978 | Sawyer | |
| 4,108,161 A | 8/1978 | Samuels et al. | |
| 4,192,293 A | 3/1980 | Asrican | |
| 4,211,325 A | 7/1980 | Wright | |
| 4,261,342 A | 4/1981 | Aranguren Duo | |

(Continued)

FOREIGN PATENT DOCUMENTS

DE   3831 540 A1   4/1989

(Continued)

OTHER PUBLICATIONS

Cohn, Jay N., M.D., *The Management of Chronic Heart Failure*, The New England Journal of Medicine, vol. 335, No. 7, pp. 490-498, August 15, 1996.

(Continued)

*Primary Examiner*—George R. Evanisko
*Assistant Examiner*—Joseph Stoklosa
(74) *Attorney, Agent, or Firm*—Fulwider Patton LLP

(57) ABSTRACT

A cardiac harness for treating a patient's heart includes elastic rows connected by a connector assembly. The connector assembly can have a specific pattern, or can be formed of elongated elastic material connecting all of the apices of adjacent rows. The connectors maintain proper spacing between rows or rings on the harness and provide longitudinal stability.

10 Claims, 14 Drawing Sheets

U.S. PATENT DOCUMENTS

| | | |
|---|---|---|
| 4,306,318 A | 12/1981 | Mano et al. |
| 4,372,293 A | 2/1983 | Vijil-Rosales |
| 4,403,604 A | 9/1983 | Wilkinson et al. |
| 4,428,375 A | 1/1984 | Ellman |
| 4,512,471 A | 4/1985 | Kaster et al. |
| 4,536,893 A | 8/1985 | Parravicini |
| 4,545,783 A | 10/1985 | Vaughn |
| 4,628,937 A | 12/1986 | Hess et al. |
| 4,630,597 A | 12/1986 | Kantrowitz et al. |
| 4,665,906 A | 5/1987 | Jervis |
| 4,690,134 A | 9/1987 | Snyders |
| 4,697,703 A | 10/1987 | Will |
| 4,750,619 A | 6/1988 | Cohen et al. |
| 4,821,723 A | 4/1989 | Baker, Jr. et al. |
| 4,827,932 A | 5/1989 | Ideker et al. |
| 4,834,707 A | 5/1989 | Evans |
| 4,838,288 A | 6/1989 | Wright et al. |
| 4,840,626 A | 6/1989 | Linsky et al. |
| 4,863,016 A | 9/1989 | Fong et al. |
| 4,878,890 A | 11/1989 | Bilweis |
| 4,936,857 A | 6/1990 | Kulik |
| 4,957,477 A | 9/1990 | Lundbäck |
| 4,960,424 A | 10/1990 | Grooters |
| 4,973,300 A | 11/1990 | Wright |
| 4,976,730 A | 12/1990 | Kwan-Gett |
| 5,031,762 A | 7/1991 | Heacox |
| 5,057,117 A | 10/1991 | Atweh |
| 5,067,957 A | 11/1991 | Jervis |
| 5,087,243 A | 2/1992 | Avitall |
| 5,098,369 A | 3/1992 | Heilman et al. |
| 5,106,386 A | 4/1992 | Isner et al. |
| 5,119,804 A | 6/1992 | Anstadt |
| 5,131,905 A | 7/1992 | Grooters |
| 5,150,706 A | 9/1992 | Cox et al. |
| 5,169,381 A | 12/1992 | Snyders |
| 5,186,711 A | 2/1993 | Epstein |
| 5,190,546 A | 3/1993 | Jervis |
| 5,192,314 A | 3/1993 | Daskalakis |
| 5,197,978 A | 3/1993 | Hess |
| 5,256,132 A | 10/1993 | Snyders |
| 5,279,539 A | 1/1994 | Bohan et al. |
| 5,290,217 A | 3/1994 | Campos |
| 5,336,254 A | 8/1994 | Brennen et al. |
| 5,344,442 A | 9/1994 | Deac |
| 5,352,184 A | 10/1994 | Goldberg et al. |
| 5,356,432 A | 10/1994 | Rutkow et al. |
| 5,366,460 A | 11/1994 | Eberbach |
| 5,383,840 A | 1/1995 | Heilman et al. |
| 5,385,156 A | 1/1995 | Oliva |
| 5,385,229 A | 1/1995 | Bittmann et al. |
| 5,385,528 A | 1/1995 | Wilk |
| 5,405,360 A | 4/1995 | Tovey |
| 5,429,584 A | 7/1995 | Chiu |
| 5,433,727 A | 7/1995 | Sideris |
| 5,456,711 A | 10/1995 | Hudson |
| 5,460,962 A | 10/1995 | Kemp |
| 5,500,015 A | 3/1996 | Deac |
| 5,507,779 A | 4/1996 | Altman |
| 5,509,428 A | 4/1996 | Dunlop |
| 5,524,633 A | 6/1996 | Heaven et al. |
| 5,533,958 A | 7/1996 | Wilk |
| 5,534,024 A | 7/1996 | Rogers et al. |
| 5,545,210 A | 8/1996 | Hess et al. |
| 5,558,617 A | 9/1996 | Heilman et al. |
| 5,571,215 A | 11/1996 | Sterman et al. |
| 5,582,616 A | 12/1996 | Bolduc et al. |
| 5,584,803 A | 12/1996 | Stevens et al. |
| 5,593,424 A | 1/1997 | Northrup, III |
| 5,593,441 A | 1/1997 | Lichtenstein et al. |
| 5,597,378 A | 1/1997 | Jervis |
| 5,603,337 A | 2/1997 | Jarvik |
| 5,607,477 A | 3/1997 | Schindler et al. |
| 5,647,372 A | 7/1997 | Tovey et al. |
| 5,647,380 A | 7/1997 | Campbell et al. |
| 5,695,525 A | 12/1997 | Mulhauser et al. |
| 5,702,343 A | 12/1997 | Alferness |
| 5,713,954 A | 2/1998 | Rosenberg et al. |
| 5,727,569 A | 3/1998 | Benetti et al. |
| 5,749,839 A | 5/1998 | Kovacs |
| 5,782,746 A | 7/1998 | Wright |
| 5,800,334 A | 9/1998 | Wilk |
| 5,800,528 A | 9/1998 | Lederman et al. |
| 5,814,097 A | 9/1998 | Sterman et al. |
| 5,824,028 A | 10/1998 | Knisley |
| 5,836,311 A | 11/1998 | Borst et al. |
| 5,848,962 A | 12/1998 | Feindt et al. |
| 5,849,005 A | 12/1998 | Garrison et al. |
| 5,853,422 A | 12/1998 | Huebsch et al. |
| 5,865,791 A | 2/1999 | Whayne et al. |
| 5,876,432 A | 3/1999 | Lau et al. |
| 5,904,690 A | 5/1999 | Middleman et al. |
| 5,910,124 A | 6/1999 | Rubin |
| 5,927,284 A | 7/1999 | Borst et al. |
| 5,948,019 A | 9/1999 | Shu et al. |
| 5,957,977 A | 9/1999 | Melvin |
| 5,961,440 A | 10/1999 | Schweich, Jr. et al. |
| 5,976,069 A | 11/1999 | Navia et al. |
| 5,979,456 A | 11/1999 | Magovern |
| 5,984,857 A | 11/1999 | Buck et al. |
| 5,990,378 A | 11/1999 | Ellis |
| 6,007,486 A | 12/1999 | Hunt et al. |
| 6,015,378 A | 1/2000 | Borst et al. |
| 6,024,096 A | 2/2000 | Buckberg |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,071,303 A | 6/2000 | Laufer |
| 6,076,013 A | 6/2000 | Brennan et al. |
| 6,077,214 A * | 6/2000 | Mortier et al. ............... 600/16 |
| 6,077,218 A | 6/2000 | Alferness |
| 6,079,414 A | 6/2000 | Roth |
| 6,085,754 A | 7/2000 | Alferness et al. |
| 6,095,968 A | 8/2000 | Snyders |
| 6,110,100 A | 8/2000 | Talpade |
| 6,117,159 A | 9/2000 | Huebsch et al. |
| 6,117,979 A | 9/2000 | Hendriks et al. |
| 6,123,662 A | 9/2000 | Alferness et al. |
| 6,125,852 A | 10/2000 | Stevens et al. |
| 6,126,590 A | 10/2000 | Alferness |
| 6,155,968 A | 12/2000 | Wilk |
| 6,155,972 A | 12/2000 | Nauertz et al. |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,165,121 A | 12/2000 | Alferness |
| 6,165,122 A | 12/2000 | Alferness |
| 6,166,184 A | 12/2000 | Hendriks et al. |
| 6,169,922 B1 | 1/2001 | Alferness et al. |
| 6,174,279 B1 | 1/2001 | Girard |
| 6,179,791 B1 | 1/2001 | Krueger |
| 6,183,411 B1 | 2/2001 | Mortier et al. |
| 6,190,408 B1 | 2/2001 | Melvin |
| 6,193,648 B1 | 2/2001 | Krueger |
| 6,206,820 B1 | 3/2001 | Kazi et al. |
| 6,214,047 B1 | 4/2001 | Melvin |
| 6,217,894 B1 | 4/2001 | Sawhney et al. |
| 6,221,103 B1 | 4/2001 | Melvin |
| 6,224,540 B1 | 5/2001 | Lederman et al. |
| 6,230,714 B1 | 5/2001 | Alferness et al. |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,282,445 B1 | 8/2001 | Reinhardt et al. |
| 6,287,250 B1 | 9/2001 | Peng et al. |

| | | |
|---|---|---|
| 6,293,906 B1 | 9/2001 | Vanden Hoek et al. |
| 6,306,141 B1 | 10/2001 | Jervis |
| 6,312,725 B1 | 11/2001 | Wallace et al. |
| 6,352,710 B2 | 3/2002 | Sawhney et al. |
| 6,360,749 B1 | 3/2002 | Jayaraman |
| 6,375,608 B1 | 4/2002 | Alferness |
| 6,390,976 B1 | 5/2002 | Spence et al. |
| 6,402,679 B1 | 6/2002 | Mortier et al. |
| 6,402,680 B2 | 6/2002 | Mortier et al. |
| 6,406,420 B1 | 6/2002 | McCarthy et al. |
| 6,409,760 B1 | 6/2002 | Melvin |
| 6,416,459 B1 | 7/2002 | Haindl |
| 6,425,856 B1 | 7/2002 | Shapland et al. |
| 6,432,039 B1 | 8/2002 | Wardle |
| 6,451,025 B1 | 9/2002 | Jervis |
| 6,482,146 B1 | 11/2002 | Alferness et al. |
| 6,517,570 B1 | 2/2003 | Lau et al. |
| 6,537,203 B1 | 3/2003 | Alferness et al. |
| 6,544,168 B2 | 4/2003 | Alferness |
| 6,547,821 B1 | 4/2003 | Taylor et al. |
| 6,564,094 B2 | 5/2003 | Alferness et al. |
| 6,567,699 B2 | 5/2003 | Alferness et al. |
| 6,569,082 B1 | 5/2003 | Chin |
| 6,572,533 B1 | 6/2003 | Shapland et al. |
| 6,575,921 B2 | 6/2003 | Vanden Hoek et al. |
| 6,582,355 B2 | 6/2003 | Alferness et al. |
| 6,587,734 B2 | 7/2003 | Okuzumi |
| 6,595,912 B2 | 7/2003 | Lau et al. |
| 6,602,184 B2 | 8/2003 | Lau et al. |
| 6,612,978 B2 | 9/2003 | Lau et al. |
| 6,612,979 B2 | 9/2003 | Lau et al. |
| 6,633,780 B1 | 10/2003 | Berger |
| 6,645,139 B2 | 11/2003 | Haindl |
| 6,663,558 B2 | 12/2003 | Lau et al. |
| 6,673,009 B1 | 1/2004 | Vanden Hoek et al. |
| 6,682,474 B2 | 1/2004 | Lau et al. |
| 6,682,475 B2 | 1/2004 | Cox et al. |
| 6,682,476 B2 | 1/2004 | Alferness et al. |
| 6,685,620 B2 | 2/2004 | Gifford, III et al. |
| 6,685,627 B2 | 2/2004 | Jayaraman |
| 6,689,048 B2 | 2/2004 | Vanden Hoek et al. |
| 6,695,769 B2 | 2/2004 | French et al. |
| 6,699,259 B2 | 3/2004 | Fogarty et al. |
| 6,701,929 B2 | 3/2004 | Hussein |
| 6,702,732 B1 | 3/2004 | Lau et al. |
| 6,723,041 B2 | 4/2004 | Lau et al. |
| 6,730,016 B1 | 5/2004 | Cox et al. |
| 6,755,779 B2 | 6/2004 | Vanden Hoek et al. |
| 6,759,431 B2 | 7/2004 | Hunter et al. |
| 6,818,018 B1 | 11/2004 | Sawhney |
| 6,833,408 B2 | 12/2004 | Sehl et al. |
| 6,876,887 B2 | 4/2005 | Okuzumi |
| 6,881,185 B2 | 4/2005 | Vanden Hock et al. |
| 6,887,192 B1 | 5/2005 | Whayne et al. |
| 6,893,392 B2 | 5/2005 | Alferness |
| 6,896,652 B2 | 5/2005 | Alferness et al. |
| 6,902,522 B1 | 6/2005 | Walsh et al. |
| 6,902,524 B2 | 6/2005 | Alferness et al. |
| 6,908,426 B2 | 6/2005 | Shapland et al. |
| 7,181,272 B2 * | 2/2007 | Struble et al. .................. 607/4 |
| 2001/0029314 A1 | 10/2001 | Alferness et al. |
| 2001/0047122 A1 | 11/2001 | Vanden Hoek et al. |
| 2002/0007216 A1 | 1/2002 | Melvin |
| 2002/0022880 A1 | 2/2002 | Melvin |
| 2002/0045798 A1 * | 4/2002 | Lau et al. ..................... 600/37 |
| 2002/0068849 A1 | 6/2002 | Schweich, Jr. et al. |
| 2002/0077524 A1 | 6/2002 | Schweich, Jr. et al. |
| 2002/0082647 A1 | 6/2002 | Alferness et al. |
| 2002/0091296 A1 | 7/2002 | Alferness |
| 2002/0103511 A1 | 8/2002 | Alferness et al. |
| 2002/0151950 A1 | 10/2002 | Okuzumi |
| 2003/0060674 A1 | 3/2003 | Gifford, III et al. |
| 2003/0060677 A1 | 3/2003 | French et al. |
| 2003/0060895 A1 | 3/2003 | French et al. |
| 2003/0199733 A1 | 10/2003 | Shapland et al. |
| 2003/0199955 A1 | 10/2003 | Struble et al. |
| 2003/0229265 A1 | 12/2003 | Girard et al. |
| 2004/0133069 A1 | 7/2004 | Shapland et al. |
| 2004/0171907 A1 | 9/2004 | Alferness et al. |
| 2004/0171908 A1 | 9/2004 | Alferness et al. |
| 2005/0059854 A1 | 3/2005 | Hoek et al. |
| 2005/0085688 A1 | 4/2005 | Girard et al. |

FOREIGN PATENT DOCUMENTS

| | | |
|---|---|---|
| DE | 38 31 540 C2 | 6/1993 |
| DE | 295 17 393 U1 | 3/1996 |
| EP | 0 370 931 A1 | 5/1990 |
| EP | 0 280 564 B1 | 6/1993 |
| EP | 0 583 012 B1 | 7/1996 |
| EP | 0 791 330 A3 | 8/1997 |
| EP | 0 919 193 A1 | 6/1999 |
| FR | 2 527 435 | 12/1983 |
| FR | 2 645 739 | 10/1990 |
| GB | 2 115 287 A | 9/1983 |
| GB | 2 209 678 A | 5/1989 |
| JP | 60-203250 | 10/1985 |
| JP | 1-145066 | 6/1989 |
| JP | 1-271829 | 10/1989 |
| SU | 1009457 | 4/1983 |
| SU | 3316206/28-13 | 4/1983 |
| SU | 1734767 A1 | 5/1992 |
| WO | WO 91/19465 | 12/1991 |
| WO | WO 95/06447 | 3/1995 |
| WO | WO 96/04852 | 2/1996 |
| WO | WO 96/40356 | 12/1996 |
| WO | WO 97/20505 | 6/1997 |
| WO | WO 97/24101 | 7/1997 |
| WO | WO 98/03213 | 1/1998 |
| WO | WO 98/14136 | 4/1998 |
| WO | WO 98/26738 | 6/1998 |
| WO | WO 98/29041 | 7/1998 |
| WO | WO 98/58598 | 12/1998 |
| WO | WO 00/02500 | 1/1999 |
| WO | WO 99/11201 | 3/1999 |
| WO | WO 99/30647 | 6/1999 |
| WO | WO 99/44534 | 9/1999 |
| WO | WO 99/44680 | 9/1999 |
| WO | WO 99/53977 | 10/1999 |
| WO | WO 99/56655 | 11/1999 |
| WO | WO 00/06026 | 2/2000 |
| WO | WO 00/06027 | 2/2000 |
| WO | WO 00/06028 | 2/2000 |
| WO | WO 00/13722 | 3/2000 |
| WO | WO 00/16700 | 3/2000 |
| WO | WO 00/18320 | 4/2000 |
| WO | WO 00/28912 | 5/2000 |
| WO | WO 00/28918 | 5/2000 |
| WO | WO/0036995 | 6/2000 |
| WO | WO 00/42919 | 7/2000 |
| WO | WO 00/45735 | 8/2000 |
| WO | WO 00/48795 | 8/2000 |
| WO | WO 00/62727 | 10/2000 |
| WO | WO 00/74769 | 12/2000 |
| WO | WO 01/17437 | 3/2001 |
| WO | WO 01/21098 | 3/2001 |
| WO | WO 01/50981 | 7/2001 |
| WO | WO 01/67985 | 9/2001 |
| WO | WO 01/85061 | 11/2001 |
| WO | WO 01/91667 | 12/2001 |
| WO | WO 01/95830 | 12/2001 |
| WO | WO 01/95831 | 12/2001 |
| WO | WO 01/95832 | 12/2001 |
| WO | WO 02/13726 | 2/2002 |
| WO | WO 02/19917 | 3/2002 |
| WO | WO 03/026483 | 4/2003 |

| | | |
|---|---|---|
| WO | WO 03/026484 | 4/2003 |
| WO | WO 03/026485 | 4/2003 |

OTHER PUBLICATIONS

Zhou, Xiaohong, et al., *Epicardial Mapping of Ventricular Defibrillation With Monophasic and Biphasic Shocks in Dogs*, Circulation Research, vol. 72, No. 1, pp. 145-160, Jan. 1993.

Shorofsky, Stephen R., et al., *Comparison of Step-Down and Binary Search Algorithms for Determination of Defibrillation Threshold in Humans*, PACE, vol. 27, pp. 218-220, Feb. 2004.

Gold, Michael R., M.D., et al., *Comparison of Single- and Dual-Coil Active Pectoral Defibrillation Lead Systems*, Journal of the American College of Cardiology, vol. 31, No. 6, pp. 1391-1394, May 1998.

Rinaldi, C. Aldo, *A Randomized Prospective Study of Single Coil Versus Dual Coil Defibrillation in Patients With Ventricular Arrhythmias Undergoing Implantable Cardioverter Defibrillator Therapy*, PACE, vol. 26, pp. 1684 1690, Aug. 2003.

Schwartzman, David, M.D., et al., *Serial Defibrillation Lead Impedance in Patients with Epicardial and Nonthoracotomy Lead Systems*, Journal of Cardiovascular Electrophysiology, vol. 7, No. 8, pp. 697-703, Aug. 1996.

Sandstedt, Bengt, et al., *Bidirectional Defibrillation Using Implantable Defibrillators: A Prospective Randomized Comparison Between Pectoral and Abdominal Active Generators*, PACE, vol. 24, Part I, pp. 1343-1353, Sep. 2001.

Schulte, B., et al., *Dual-Coil vs. Single-Coil Active Pectoral Implantable Defibrillator Lead Systems: Defibrillation Lead Requirements and Probability of Defibrillation Success at Multiples of the Defibrillation Energy Requirements*, Europace, vol. 3, pp. 177-180, Jul. 2001.

U.S. Appl. No. 09/952,145, filed Sep. 10, 2001 published on Feb. 14, 2003 as Pub. No. 02-0019580-A1; Inventors: Lau et al.

U.S. Appl. No. 10/314,696, filed Dec. 9, 2002 published on Apr. 3, 2003 as Pub. No. 03-0065248-A1; Inventors: Lau et al.

U.S. Appl. No. 60/486,062, filed Jul. 10, 2003; Inventors: Hong et al.

U.S. Appl. No. 10/698,237, filed Oct. 31, 2003 published on Jul. 29, 2004 as Pub. No. 04-0147805-A1; Inventor: Lau.

U.S. Appl. No. 10/704,376, filed Nov. 7, 2003; Inventor: Lau.

U.S. Appl. No. 10/715,150, filed Nov. 17, 2003 published on Mar. 10, 2005 as Pub. No. 05-0055032; Inventor: Lau.

U.S. Appl. No. 60/535,888, filed Jan. 12, 2004; Inventors: Fishler et al.

Bencini, Adriano, M.D., *The "Pneumomassage" of the Heart*, Surgery, vol. 39, No. 3, Mar. 1956.

Anstadt, George L., et al., *A New Instrument for Prolonged Mechanical Cardiac Massage*, Abstracts of the 38th Scientific Sessions, Supplement II to Circulation, vols. 31 and 32, pp. 375-384, Oct. 1965.

Lev, Maurice, M.D., et al., *Single (Primitive) Ventricle*, Circulation, vol. 39, pp. 577-591.

Paling, D.F., *Warp Knitting Technology*, 1970.

Edie, Richard N., M.D., et al., *Surgical Repair of Single Ventricle*, The Journal of Thoracic and Cardiovascular Surgery, vol. 66, No. 3, pp. 350-360, Sep. 1972.

McGoon, Dwight C., M.D., et al., *Correction of the Univentricular Heart Having Two Atriovantricular Valves*, The Journal of Thoracic and Cardiovascular Surgery, vol. 74, No. 2, pp. 218-226, Aug. 1977.

Doty, Donald B., et al., *Septation of the Univentricular Heart: Transatrial Approach*, The Journal of Thoracic and Cardiovascular Surgery, vol. 78, No. 3, pp. 424-430, Sep. 1979.

Schetky, L. McDonald, *Shap- Memory Alloys*, Scientific American, vol. 241, No. 5, pp. 74-82, Nov. 1979.

Melton, K.N., et al., *Alloys With Two-Shape Memory Effect*, Mechanical Engineering, pp. 42-43, Mar. 1980.

Feldt, Robert H., M.D., et al., *Current Status of the Septation Procedure for Univentricular Heart*, The Journal of Thoracic and Cardiovascular Surgery, vol. 82, No. 1, pp. 93-97, Jul. 1981.

Carpentier, A., et al., *Myocardial Substitution With Stimulated Skeletal Muscle: First Successful Clinical Case*, The Lancet, Jun. 1, 1985.

Anstadt, George L. et al., *Direct Mechanical Ventricular Actuation: A Review*, Resuscitation, pp. 7-23, 1991.

Anstadt, Mark P., M.D., et al., *Pulsatile Reperfusion After Cardiac Arrest Improves Neurologic Outcome*, American Surgery, vol. 214, No. 4, pp. 478-490, Oct. 1991.

Schumacker, Harris B., Jr., *Chapter 21: Cardiac Aneurysms, The Evolution of Cardiac Surgery*, pp. 159-165, 1992.

Savage, Edward B., M.D., et al., *Repair of Left Ventricular Aneurysm*, The Journal of Thoracic and Cardiovascular Surgery, vol. 104, No. 3, pp. 752-762, Sep. 1992.

Carpentier, Alain, M.D., Ph.D., et al., *Dynamic Cardiomyoplasty at Seven Years*, The Journal of Thoracic and Cardiovascular Surgery, vol. 106, No. 1, pp. 42-54, Jul. 1993.

Capouya, Eli R., M.D., et al., *Girdling Effect of Nonstimulated Cardiomyoplasty on Left Ventricular Function*, Annals of Thoracic Surgeons, vol. 56, pp. 867-871, 1993.

Chekanov, Valeri, M.D., Ph.D., *Nonstimulated Cardiomyoplasty Wrap Attenuated the Degree of Left Ventricular Enlargement*, Annals of Thoracic Surgeons, vol. 57, pp. 1684-1690, 1997.

Chiu, Ray C.-J, *Using Skeletal Muscle for Cardiac Assistance*, Scientific American, pp. 68-77, Nov./Dec. 1994.

Kass, David A., M.D., et al., *Reverse Remodeling From Cardiomyoplasty in Human Heart Failure: External Constraint Versus Active Assist*, Circulation, vol. 91, No. 9, pp. 2314-2318, May 1, 1995.

Vaynblat, Mikhail, M.D., et al., *Cardiac Binding in Experimental Heart Failure*, Annals of Thoracic Surgery (Abstract), Supplement to Circulation, vol. 92, Suppl. 1, 1995.

Levin, Howard R., M.D., et al., *Reversal of Chronic Ventricular Dilation in Patients With End-Stage Cardiomyopathy by Prolonged Mechanical Unloading*, Circulation, vol. 91, No. 11, pp. 2717-2720, 1995.

Chaudhry, Pervaiz A., M.D., et al., *Acute Ventricular Reduction with Acorn's Cardiac Support Device Prevents Progressive Left Ventricular Dysfunction and Remodeling in Dogs With Advanced Heart Failure*, Cardiothoracic Surgery, pp. 146-148, 1996.

Oh, Joong Hwan, M.D., et al., *Mechanisms of Dynamic Cardiomyoplasty: Current Concepts*, Journal of Cardiac Surgery, vol. 11, pp. 194-199, 1996.

Badhwar, Vinay, *Power Generation From Four Skeletal Muscle Configurations Design Implications for a Muscle Powered Cardiac Assist Device*, ASAIO Journal, vol. 43, pp. M651-M657, 1997.

Westaby, Stephen, et al., *Landmarks in Cardiac Surgery*, pp. 198-199, 1997.

Cox, James L., *Left Ventricular Aneurysms: Pathophysiologic Observations and Standard Resection*, Seminars in Thoracic and Cardiovascular Surgery, vol. 9, No. 2, pp. 113-122, Apr. 1997.

Coletta, C., et al., *Prognostic Value of Left Ventricular Volume Response During Dobutamine Stress Echocardiography*, European Heart Journal, vol. 18, pp. 1559-1603, Oct. 1997.

Capomolla, Soccorso, M.D., et al., *Dobutamine and Nitroprusside Infusion in Patients With Severe Congestive Heart Failure: Hemodynamic Improvement by Discordant Effects on Mitral Regurgitation, Left Atrial Function, and Ventricular Function*, American Heart Journal, 1089-1098, Dec. 1997.

Oh, Joong Hwan, *The Effects of Prosthetic Cardiac Binding and Adyanmic Cardiomyoplasty in a Model of Dilated Cardiomyopathy*, The Journal of Thoracic and Cardiovascular Surgery, vol. 116, No. 1, pp. 148-153, 1998.

Cohn, Jay N., M.D., *Preventing Congestive Heart Failure*, American Family Physician, 6 pages, Apr. 15, 1998.

Cohn, Jay N., M.D., *Structural Basis for Heart Failure: Ventricular Remodeling and Its Pharmacological Inhibition*, Circulation, vol. 91, No. 10, pp. 2504-2507, May 15, 1995.

Guadron, Peter, M.D., et al., *Progressive Left Ventricular Dysfunction and Remodeling After Myocardial Infarction*, Circulation, vol. 87, pp. 755-763, Mar. 1993.

Pfeiffer, Marc A., M.D., et al., *Ventricular Remodeling After Myocardial Infarction: Experimental Observations and Clinical Implications*, Circulation, vol. 81, No. 4, pp. 1161-1172, Apr. 1990.

Guasp, Francisco Torrent, *Una protesis contentiva para el traiamiento de le microcardiopatia dilatads*, Revista Españo la de Cardiologia, vol. 51, No. 7, Jul. 1998.

Power, J.M., et al., *Passive Ventricular Constraint Amends the Course of Heart Failure: A Study in an Ovine Model of Dilated Cardiomyopathy*, Cardiovascular Research, vol. 44, pp. 549-555, 1999.

Frazier, O.H., M.D., et al., *Left Ventricular Assist System as a Bridge to Myocardial Recovery*, Annals of Thoracic Surgery, vol. 68, pp. 734-741, 1999.

Melvin, David B., *Ventricular Radium Reduction Without Resection: A Computational Analysis*, ASAIO Journal, pp. 160-165, 1999.

ABSTRACT—Heart Failure, JACC Feb. 1999.

Raman, Jai S., FRACS, et al., *Ventricular Containment as an Adjunctive Procedure in Ischemic Cardiomyopathy: Early Results*, Annals of Thoracic Surgery, vol. 70, pp. 1124-1126, Jan. 2000.

McCarthy, Patrick M., et al., *Device Based Left Ventricular Shape Change Immediately Reduces Left Ventricular Volume and Increases Ejection Fraction in a Pacing Induced Cardiomyopathy Model in Dogs*, JACC, Feb. 2000.

Chaudhry, Pervaiz A., M.D., et al., *Passive Epicardial Containment Prevents Ventricular Remodeling in Heart Failure*, Annals of Thoracic Surgeons, vol. 70, pp. 1275-1280, 2000.

Acorn Cardiovascular, Inc., *CSD Specifications Acorn Cardiac Support Device*, 2000.

*Heart "jacket" could help stop heart failure progression*, Clinicia, No. 916, Jul. 2000.

Acorn Cardiovascular, Inc., *CorCap™ Cardiac Support Device* Pamphlet, Jun. 2001.

*Medtronic's InSync Cardiac Resynchronization Therapy Device Approved by FDA*, (Press Release) Aug. 28, 2001.

Oz, Mehmet C., M.D., *Passive Ventricular Constraint for the Treatment of Congestive Heart Failure*, Annals of Thoracic Surgery, vol. 71, pp. 5185-5187, 2001.

Abstract Supplement, *European Heart Journal*, vol. 22, Sep. 2001.

Gorman, J., *Self-Sutures: New Material Knots Up On Its Own*, Science News, vol. 161, p. 262, Apr. 27, 2002.

Teckell-Taylor, Leah A., et al., *Passive Ventricular Restraint With Nitinol Mesh Attenuates Remodeling Following Acute Myocardial Infarction*, Abstract, American College of Cardiology, undated.

Mann, Douglas L., M.D., *Basic Mechanisms of Remodeling and Reverse Remodeling*, presented at 6th Annual Scientific Meeting of the Heart Failure Society of America, Sep. 24, 2002.

Bocchi, Edimar a., M.D., *Arrhythmias and Sudden Death After Dynamic Cardiomyoplasty*, Circulation, vol. 90, No. 5, Part 2, pp. 11-107 thru 11-111, Nov. 1994.

Chachques, Juan C., M.D., *Study of Muscular and Ventricular Function in Dynamic Cardiomyoplasty: A Ten-Year Follow-Up*, The Journal of Heart and Lung Transplantation, vol. 16, No. 8, pp. 854-868, Aug. 1997.

Dullum, Mercedes K.C., M.D., et al., *Less Invasive Surgical Management of Heart Failure by Cardiac Support Device Implantation on the Beating Heart*, The Heart Surgery Forum, #2001-1818, pp. 361-363, Jan. 4-7, 2001.

Macris, Michael P. M.D., et al., *Minimally Invasive Access of the Norman Preicardium: Initial Clinical Experience with a Novel Device*, Clinical Cardiology, vol. 22 (Suppl. I), pp. I-36 thru I-39, 1999.

Thakur, Ranjan K., M.D., et al., *Latissimus Dorsi Dynamic Cardiomyoplasty: Role of Combined ICD Implantation*, Journal of Cardiac Surgery, vol. 10, pp. 295-297, 1995.

Wharton, J. Marcus, et al., *Electrophysiological Effects of Monophasic and Biphasic Stimuli in Normal and Infarcted Dogs*, PACE, vol. 13, pp. 1158-1172, Sep. 1990.

Shabetai, Ralph, *The Role of the Pericardium in the Pathophysiology of Heart Failure*, Congestive Heart Failure, Second Edition, Chapter 9, pp. 157-187, 2000.

U.S. Appl. No. 09/952,145, filed Sep. 10, 2001 published on Feb. 14, 2003 as Pub. No. 02-0019580-A1.

U.S. Appl. No. 10/314,696, filed Dec. 9, 2002 published on Apr. 3, 2003 as Pub. No. 03-0065248-A1.

U.S. Appl. No. 60/486,062, filed Jul. 10, 2003.

U.S. Appl. No. 10/698,237, filed Oct. 31, 2003 published on Jul. 29, 2004 as Pub. No. 04-0147805-A1.

U.S. Appl. No. 10/704,376, filed Nov. 7, 2003.

U.S. Appl. No. 10/715,150, filed Nov. 17, 2003.

U.S. Appl. No. 60/535,888, filed Jan. 12, 2004.

\* cited by examiner

US 7,282,024 B2

CARDIAC HARNESS HAVING INTERCONNECTED STRANDS

CROSS-REFERENCE TO RELATED APPLICATIONS

This application depends for priority upon U.S. Provisional Application No. 60/535,888 filed Jan. 12, 2004, which is incorporated herein in its entirety by reference.

FIELD OF THE INVENTION

The present invention relates to a device for treating heart failure. More specifically, the invention relates to a cardiac harness configured to be fit around at least a portion of a patient's heart. The cardiac harness includes multiple elastic rows or undulating strands extending circumferentially around the heart and connected together by a connector assembly.

BACKGROUND OF THE INVENTION

Congestive heart failure ("CHF") is characterized by the failure of the heart to pump blood at sufficient flow rates to meet the metabolic demand of tissues, especially the demand for oxygen. One characteristic of CHF is remodeling of at least portions of a patient's heart. Remodeling involves physical change to the size, shape and thickness of the heart wall. For example, a damaged left ventricle may have some localized thinning and stretching of a portion of the myocardium. The thinned portion of the myocardium often is functionally impaired, and other portions of the myocardium attempt to compensate. As a result, the other portions of the myocardium may expand so that the stroke volume of the ventricle is maintained notwithstanding the impaired zone of the myocardium. Such expansion may cause the left ventricle to assume a somewhat spherical shape.

Cardiac remodeling often subjects the heart wall to increased wall tension or stress, which further impairs the heart's functional performance. Often, the heart wall will dilate further in order to compensate for the impairment caused by such increased stress. Thus, a cycle can result, in which dilation leads to further dilation and greater functional impairment.

Historically, congestive heart failure has been managed with a variety of drugs. Devices have also been used to improve cardiac output. For example, left ventricular assist pumps help the heart to pump blood. Multi-chamber pacing has also been employed to optimally synchronize the beating of the heart chambers to improve cardiac output. Various skeletal muscles, such as the latissimus dorsi, have been used to assist ventricular pumping. Researchers and cardiac surgeons have also experimented with prosthetic "girdles" disposed around the heart. One such design is a prosthetic "sock" or "jacket" that is wrapped around the heart.

What has been needed, and is currently unavailable, is a cardiac harness having multiple elastic strands or rows interconnected by a connector assembly that prevents the longitudinal migration of the rows after the cardiac harness is mounted on the patient's heart.

SUMMARY OF THE INVENTION

The present invention relates generally to a cardiac harness that is configured to fit at least a portion of a patient's heart. The cardiac harness includes adjacent rows that are connected to one another by one or more connectors. The connectors help to maintain the position of the elastic rows relative to one another. In one embodiment, the connectors form a connector assembly between the adjacent rows of the cardiac harness. The connector assembly has a pattern that provides longitudinal stability between the adjacent rows so that the rows do not expand or shift longitudinally while mounting the harness on the heart or during use after the harness is mounted on the heart.

In another embodiment, an elongated connector is woven through the apices of adjacent rows to again maintain the spacing between the rows during delivery and use of the cardiac harness. Typically, the connectors are formed from an elastomeric material, preferably silicone rubber.

The connectors are formed by placing the undulating strands or rows in a mold and injecting the elastomeric material through the gates in the mold to form the connectors. Typically, the connectors extend between the apices of adjacent rows so that the elastomeric material formed in the mold flows around the apices of adjacent rows. Preferably, the elastomer is a silicone rubber or similar material.

DETAILED DESCRIPTION OF THE PREFERRED EMBODIMENTS

The present invention relates to a method and apparatus for treating heart failure. As discussed in Applicants' co-pending application entitled "Expandable Cardiac Harness For Treating Congestive Heart Failure," Ser. No. 09/634,043, which was filed on Aug. 8, 2000, now U.S. Pat. No. 6,702,732 issued Mar. 9, 2004, the entirety of which is hereby expressly incorporated by reference herein, it is anticipated that remodeling of a diseased heart can be resisted or even reversed by alleviating the wall stresses in such a heart. The present application discusses certain embodiments and methods for supporting the cardiac wall. Additional embodiments and aspects are also discussed in Applicants' co-pending applications entitled "Device for Treating Heart Failure," Ser. No. 10/242,016, filed Sep. 10, 2002, now U.S. Pat. No. 6,723,041 issued Apr. 20, 2004; "Heart Failure Treatment Device and Method," Ser. No. 10/287,723, filed Oct. 31, 2002; "Method and Apparatus for Supporting a Heart," Ser. No. 10/338,934, filed Jan. 7, 2003; "Cardiac Harness," Ser. No. 10/656,722, filed Sep. 5, 2003; "Cardiac Harness Delivery Device and Method," Ser. No. 10/715,150, filed Nov. 17, 2003; "Multi-Panel Cardiac Harness," Ser. No. 60/458,991, filed Mar. 28, 2003; "Self Anchoring Cardiac Harness," Ser. No. 60/486,052, filed Jul. 10, 2003; and "Cardiac Harness," Ser. No. 10/698,237, filed Oct. 31, 2003, the entirety of each of which is hereby expressly incorporate by reference.

Figure 1:
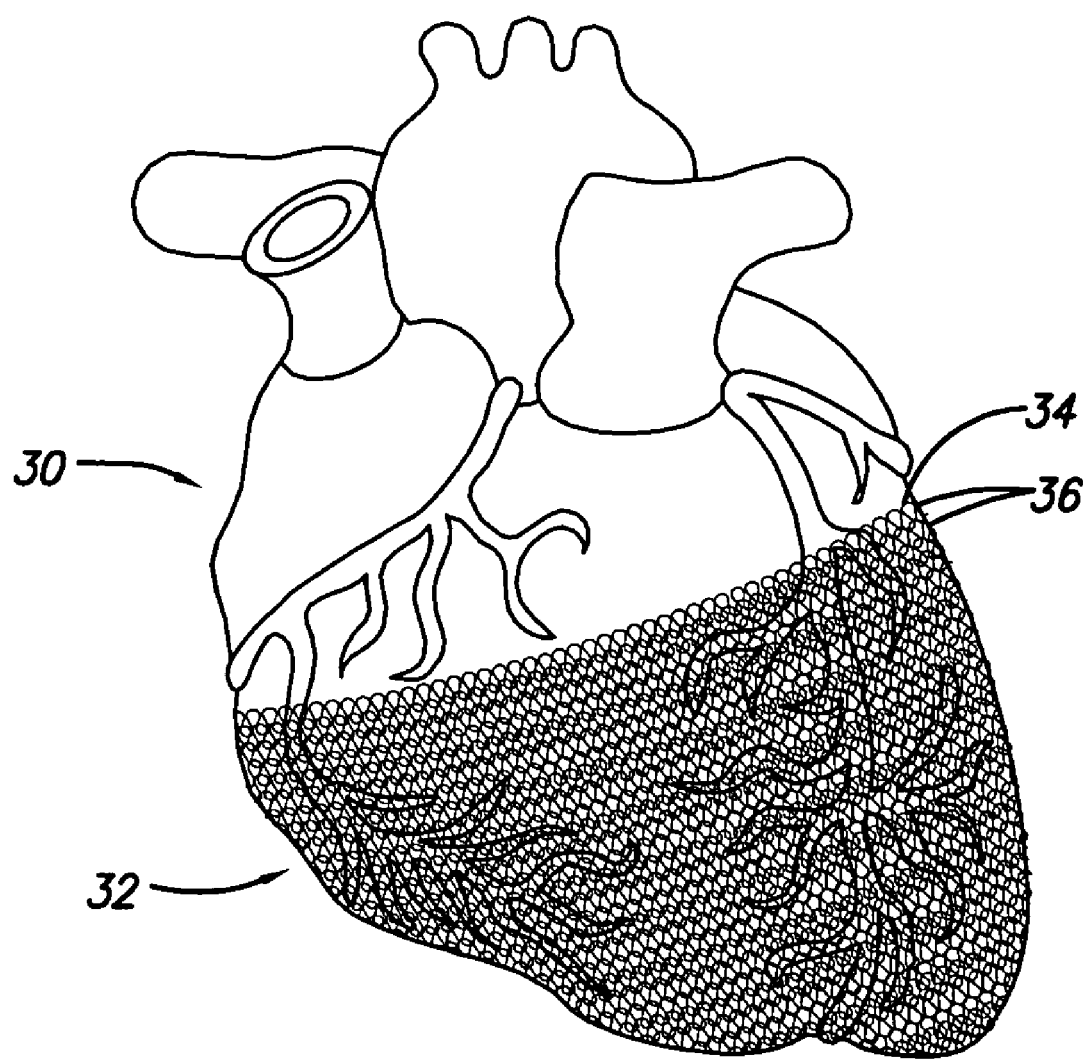
FIG. 1 depicts a schematic view of the heart with a prior art cardiac harness placed thereon.

FIG. 1 illustrates a mammalian heart 30 having a cardiac wall stress reduction device in the form of a harness 32 applied to it. The cardiac harness 32 includes rows of elastic members that circumscribe the heart 30 and, collectively, apply a mild compressive force on the heart to alleviate wall stresses.

The term "cardiac harness" as used herein is a broad term that refers to a device fit onto a patient's heart to apply a compressive force on the heart during at least a portion of the cardiac cycle. A device that is intended to be fit onto and reinforce a heart and which may be referred to in the art as a "girdle," "sock," "jacket," "cardiac reinforcement device," or the like is included within the meaning of "cardiac harness."

Figure 2A:
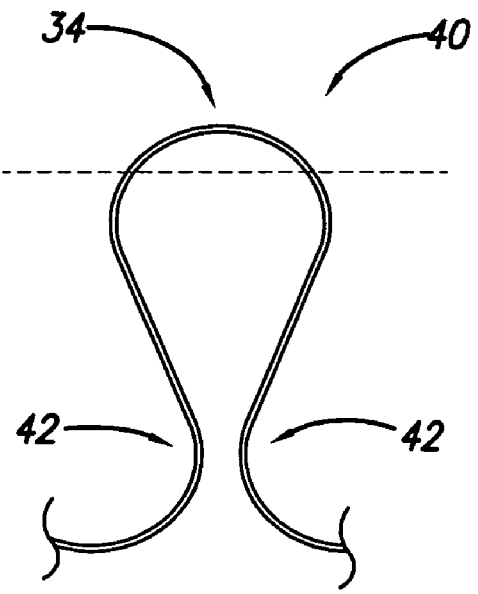
FIGS. 2A-2B depict a spring hinge of a prior art cardiac harness in a relaxed position and under tension.
Figure 2B:
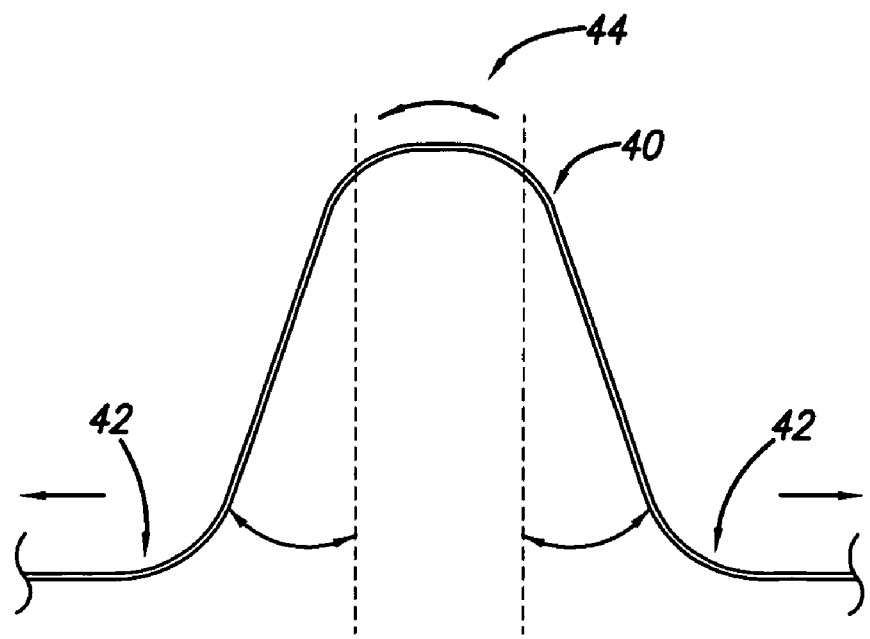

The cardiac harness 32, illustrated in FIG. 1, includes several rows or strands 36 of elastic members. Each row has a series of spring elements 34, also referred to as hinges or spring hinges, that are configured to deform as the heart 30 expands during filling. For example, FIG. 2A shows one embodiment of a hinge member 34 at rest. The hinge member 34 has a central portion 40 and a pair of arms 42. As the arms are pulled, as shown in FIG. 2B, a bending moment 44 is imposed on the central portion 40. The bending moment 44 urges the hinge member 34 back to its relaxed condition. Note that a typical row or strand has a series of such hinges, and that the hinges 34 are adapted to elastically expand and retract in the direction of the strand 36.

In the embodiment illustrated in FIG. 1, the elastic rows 36 are constructed of pulled or extruded wire that is deformed to form the spring elements. Although FIG. 1 shows adjacent rows interwoven one with another, it is to be understood that, in additional embodiments, adjacent rows may not overlay or touch one another.

Figure 3:
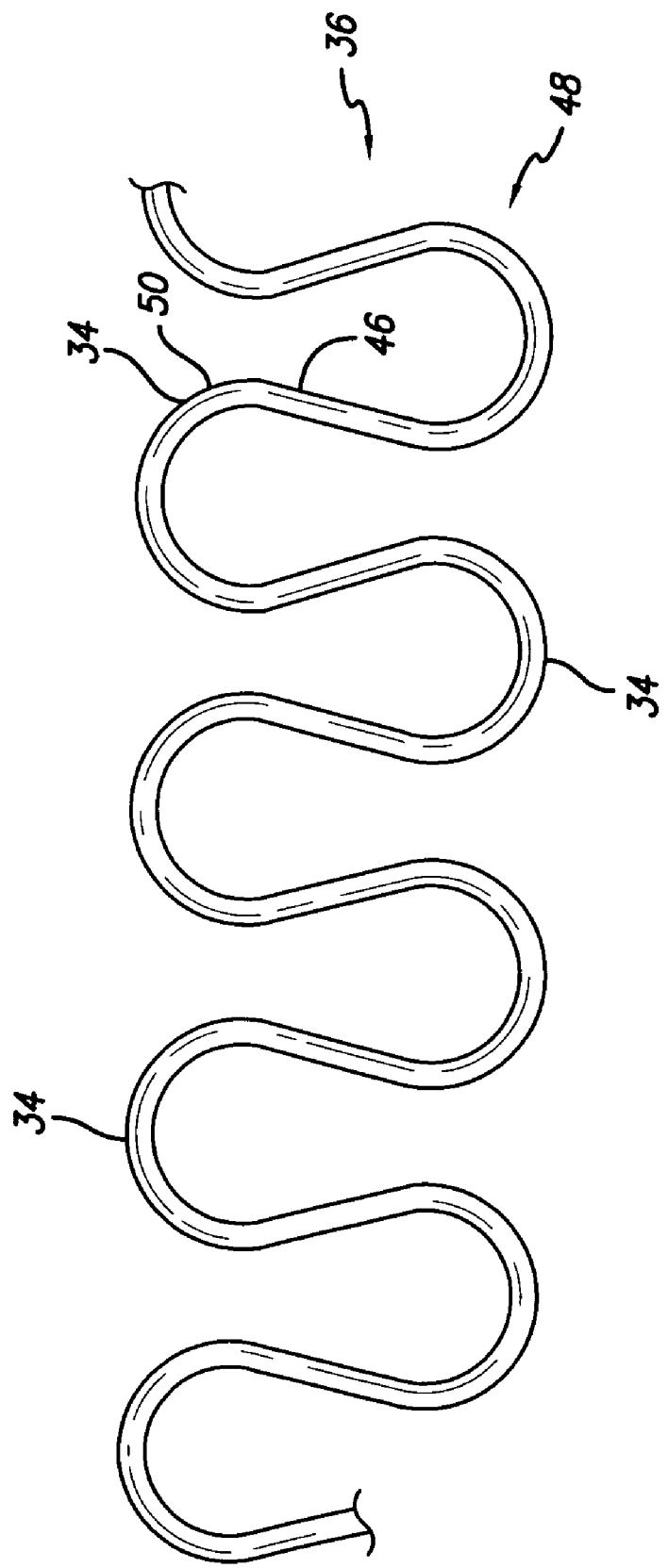
FIG. 3 depicts an unattached elongated strand or row, or series of spring elements that are coated with a dielectric material.

With next reference to FIG. 3, a close-up of a portion of one embodiment of an elastic row 36 is shown. In the illustrated embodiment, the row comprises an undulating strand of wire 46 formed into a series of successive spring elements 34. A dielectric coating 48 is disposed over the spring elements. In the illustrated embodiment, the dielectric coating comprises silicone or more precisely silicone rubber. Other acceptable materials include urethanes as well as various polymers, elastomers and the like. In the illustrated embodiment, the silicone rubber coating comprises tubing 50 that has been pulled over the wire. It is to be understood that other methods for applying a coating, such as dip coating and spraying, can also be used to apply a coating to the elastic row. Further, it should be understood that in other embodiments no coating is applied over the elastic row.

Figure 4:
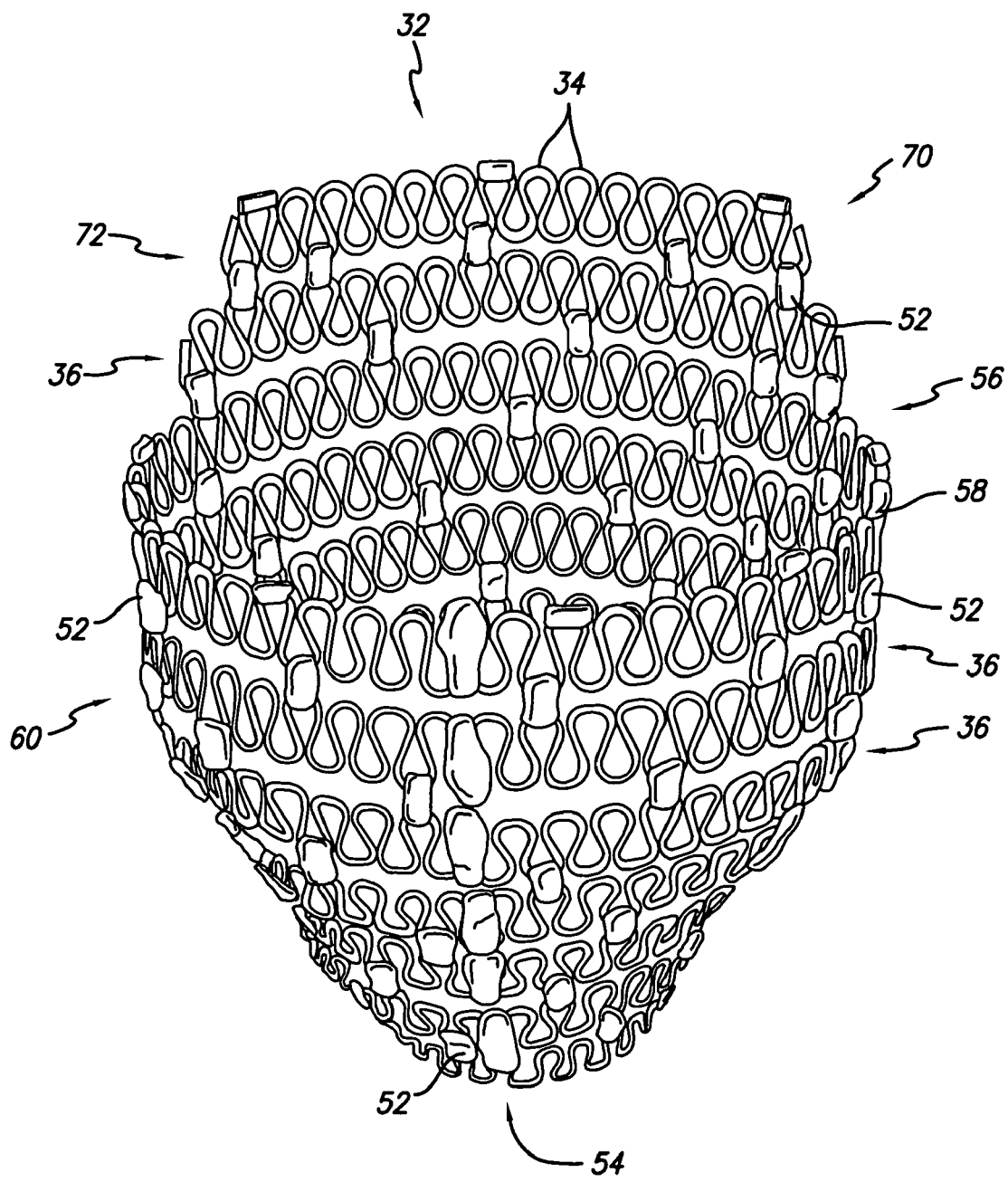
FIG. 4 depicts a perspective view of an embodiment of a cardiac harness having a plurality of rows connected by a connector assembly.

With reference next to FIG. 4, an embodiment of a cardiac harness 32 having several adjacent elastic rows 36 is illustrated. In this embodiment, adjacent rows preferably are connected to one another by one or more connectors 52. The connectors help maintain the position of the elastic rows relative to one another. Preferably, the connectors have a length oriented longitudinally relative to the elastic rows to create a space between adjacent rows. The illustrated harness is configured to circumferentially surround at least a portion of the heart between the heart apex and base portions. Preferably, the connectors allow some relative movement between adjacent rows.

The connectors 52 preferably are formed of a semi-compliant material such as silicone rubber. Most preferably the connectors are formed of the same material used for the dielectric coating 48, if applicable. Some additional materials that can be used for the conductors include, for example, medical grade polymers such as, but not limited to, polyethylene, polypropylene, polyurethane and nylon.

As discussed above, and as discussed in more detail in the applications that are incorporated herein by reference, the elastic rows 36 exert a force in resistance to expansion of the heart 30. Collectively, the force exerted by the elastic rows tends toward compressing the heart, thus alleviating wall stresses in the heart as the heart expands. Accordingly, the harness helps to decrease the workload of the heart, enabling the heart to more effectively pump blood through the patient's body and enabling the heart an opportunity to heal itself. It should be understood that several arrangements and configurations of elastic rows can be used to create a mildly compressive force on the heart to reduce wall stresses. For example, elastic members can be disposed over only a portion of the circumference of the heart or harness.

In one embodiment, each elastic row 36 initially includes an undulating elongate strand 46. During manufacturing of the cardiac harness 32, each elongate strand is cut to a length such that when opposite ends of the elongate strand are bonded together, the elongate strand assumes a ring-shaped configuration. The rings comprise the adjacent elastic rows. The lengths of the elongate strands are selected such that the resulting rings/rows are sized in conformity with the general anatomy of the patient's heart. More specifically, strands used to form the apex portion 54 of the harness are not as long as strands used to form the base portion 56. As such, and as shown in FIG. 4, the harness generally tapers from the base 56 toward the apex 54 in order to generally follow the shape of the patient's heart.

In another embodiment, the diameter of a base ring or row 58 at the base 56 of the harness 32 is smaller than the diameter of the adjacent row. In this embodiment, the harness has a greatest diameter at a point 60 between the base and apex ends 54, and tapers from that point to both the base and apex ends. Preferably, the point of greatest diameter is closer to the base end than to the apex end. It is contemplated that the lengths of the rows, as well as the sizes of the spring members 34, may be selected according to the intended size of the cardiac harness and/or the amount of compressive force the harness is intended to impart to the patient's heart.

Figure 5:
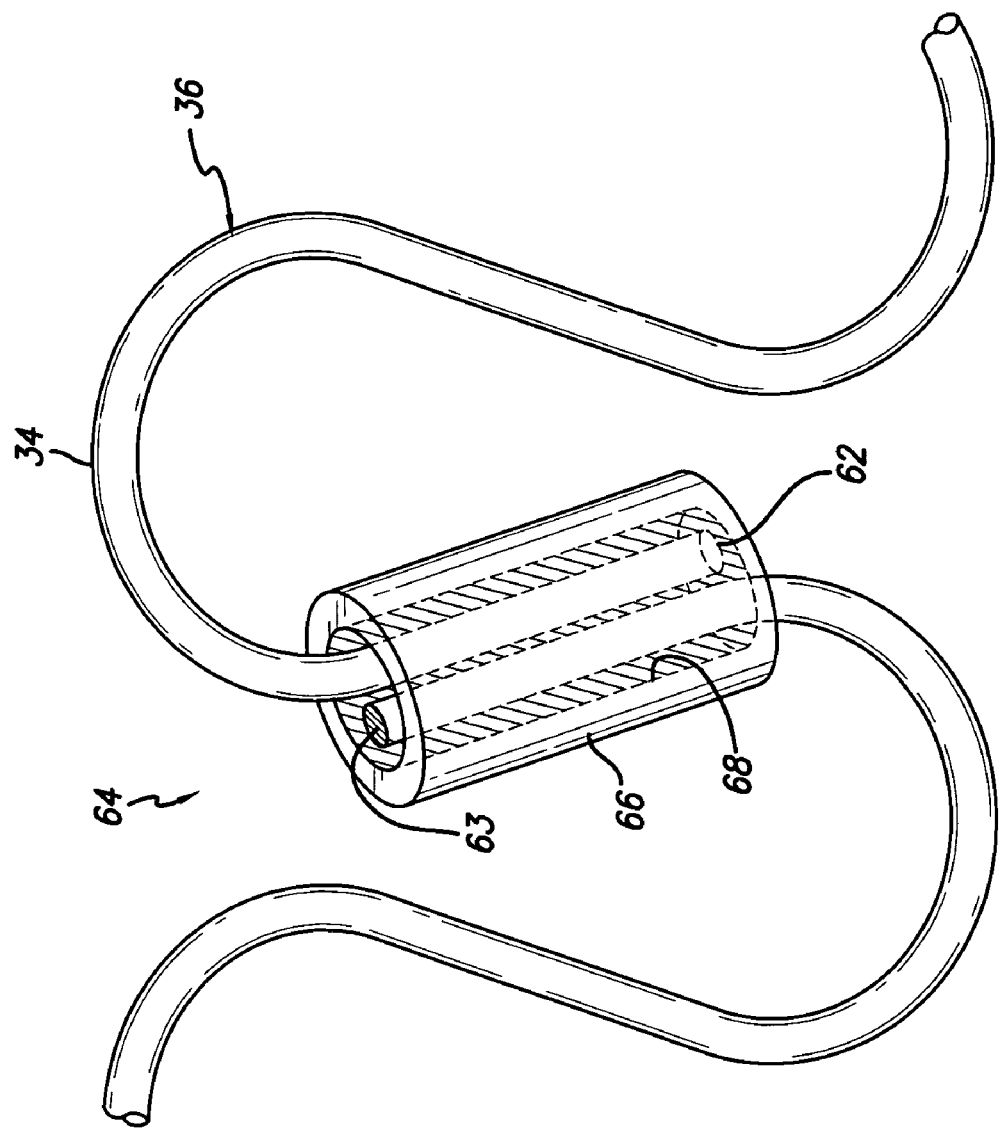
FIG. 5 depicts a portion of a elastic row showing the ends of the row being connected by a connector.
Figure 5A:
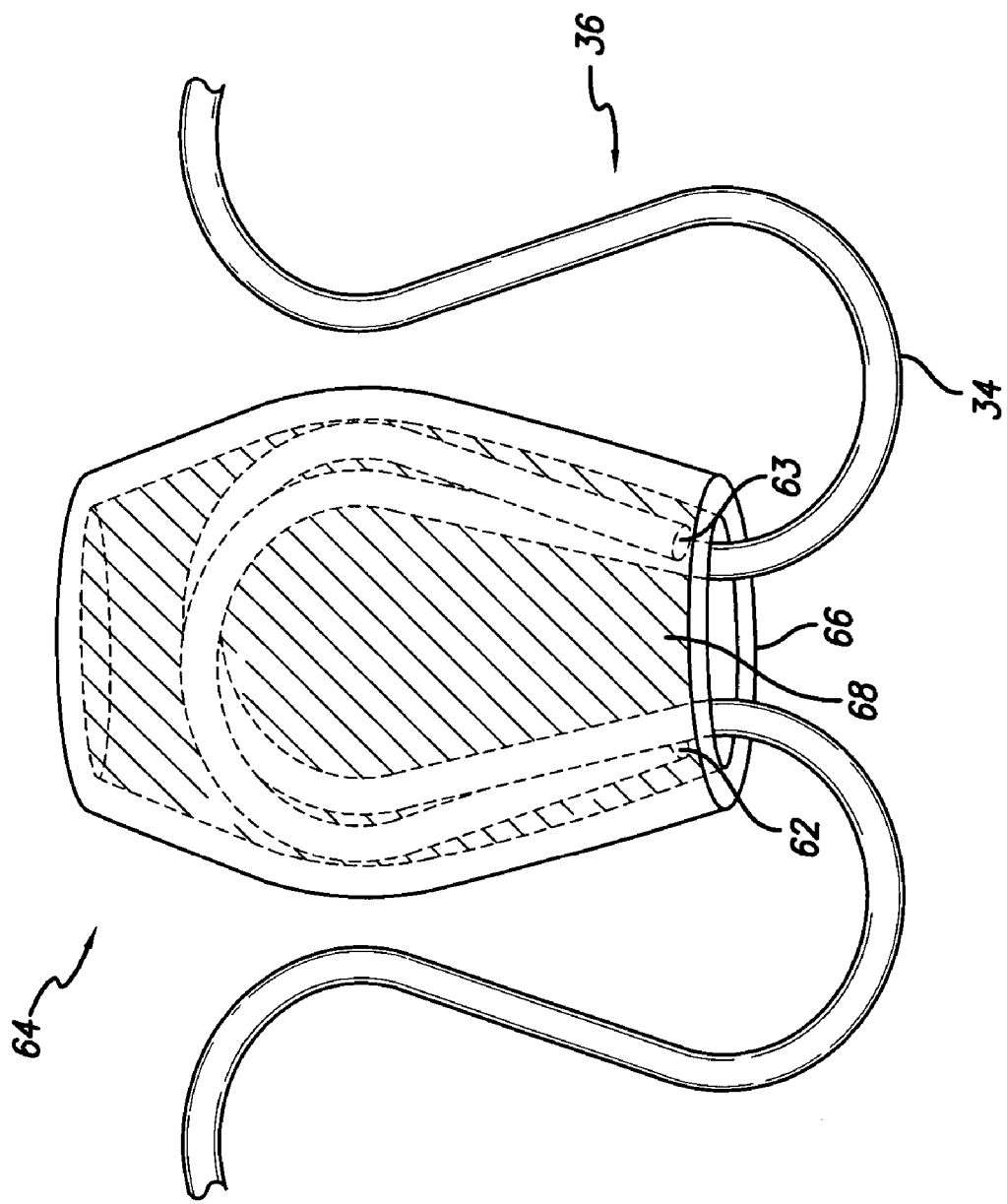
FIG. 5A depicts a portion of a row showing the ends of the row being connected by a connector.

With reference to FIG. 5, the opposite ends 62,63 of each circumferentially extending row are attached to one another by a connective junction 64. In one embodiment, illustrated in FIG. 5, each connective junction 64 includes a small tube segment 66 into which the opposite ends 62,63 of the row are inserted. The tube segment serves to prevent the opposite ends of the row from tearing loose from one another after the harness is placed on the heart. Preferably, each tube segment is filled with a dielectric material 68 such as silicone rubber, or other similar material after the row ends are placed therein. It is to be understood that additional methods and structure can be used to form the connective junction. For example, in another embodiment, illustrated in FIG. 5A, each connective junction 64 includes a small tube segment 66 into which the spring members 34 at the opposite ends 62,63 of the row 36 are inserted. The connective junction is then back-filled with a liquid silicone rubber 68 or other similar material. In still another embodiment, the ends of the strands can be welded together or intertwined. Also, in other embodiments, each ring can be unitarily formed without requiring cutting and joining of the ends.

In a still further embodiment, a cardiac harness 32 is formed by arranging one or more undulating strands 46 in a helix (not shown). In such an embodiment, portions of the helically-arranged strand are disposed adjacent one another. As with the rows/rings 36 shown in FIG. 4, connectors 52 may connect the adjacent portions. In keeping with the invention, certain aspects and principles are discussed for connecting adjacent rows/rings of a harness. It is to be understood that the same principles can be applied to a helically-arranged harness embodiment, and that adjacent portions of such a harness may be treated like adjacent rows or rings.

Due to the anatomy of the human heart, the right ventricle extends further from the apex of the heart than does the left ventricle. The cardiac harness 32 illustrated in FIG. 4 includes a right ventricle engagement portion 70 configured to fit about the uppermost portion of the right ventricle where the ventricle begins to curve inwardly. With continued reference to FIG. 4, the right ventricle engagement portion of the harness has elastic rows 36 that form only a partial row 72. Preferably, the partial rows are connected to the adjacent full row 36 in a manner so that the partial rows are at least partially stretched when the rest of the harness is at rest. As such, the partial rows are biased inwardly. When placed on the heart, the partial rows "cup" the upper portion of the right ventricle. The harness fits better and is held more securely on the heart than if the right side of the harness were configured the same as the left side.

In yet another embodiment, a cardiac harness has a basal-most row (not shown) that is less compliant than rows elsewhere in the harness. In one embodiment, the basal-most row has a larger diameter wire (not shown) than the wire of the other rows of the harness. In another embodiment, the basal-most row has a shorter length of wire (not shown) than the other rows of the harness. As such, once the cardiac harness is appropriately positioned on the heart, the basal-most row tightly engages the heart and resists apical migration of the harness. The basal-most region of the ventricles adjacent to the AV groove undergoes less circumferential change during a cardiac cycle than does the remaining bulk of the ventricles. Accordingly, it is contemplated that the basal-most row will have minimal or no adverse impact on cardiac performance, or cardiac cycle dynamics. It is also to be understood that, in other embodiments, multiple rows, or a basal-most portion of the harness, may have the reduced compliance. Such reduced compliance may be obtained in any manner. For example, in one embodiment, the basal-most portion is pre-stretched relative to the rest of the harness. In another embodiment, the basal-most portion is formed of a thicker or different material than other portions of the harness.

It is to be understood that several embodiments of cardiac harnesses can he constructed and that such embodiments may have varying configurations, sizes, flexibilities, etc. As discussed in the above-referenced applications, such harnesses can be constructed from many suitable materials including various metals, woven or knitted fabrics, plastics and braided filaments, and may or may not include elastic rows. Suitable harness materials also include superelastic materials and materials that exhibit shape memory. For example, a preferred embodiment is constructed of Nitinol. Shape memory polymers can also be employed. Such shape memory polymers can include shape memory polyurethanes or other polymers such as those containing oligo(e-caprolactone) dimethacrylate and/or poly(e-caprolactone), which are available from mnemoScience. Further, harness materials can he elastic or substantially non-elastic.

Figure 6:
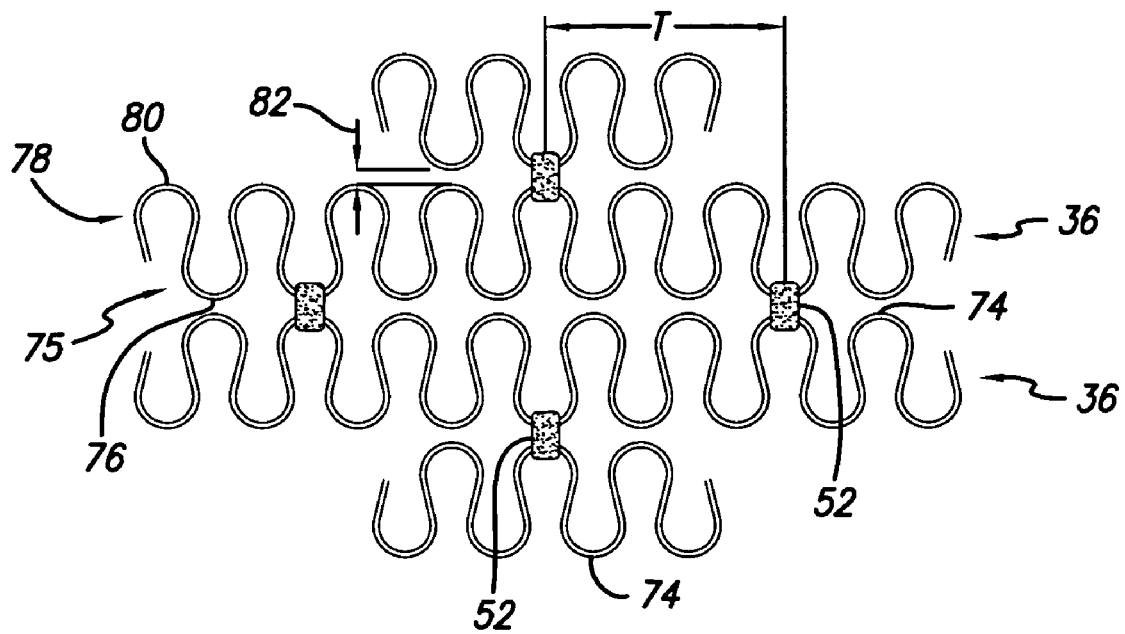
FIG. 6 depicts an enlarged partial plan view of a cardiac harness wherein the connectors provide uniform spacing between adjacent rows.

With reference to FIG. 6, a representative portion of a cardiac harness embodiment is illustrated. The illustrated portion presents a connector assembly having connectors as discussed in connection with FIG. 4. As discussed herein, the connectors interconnect adjacent rings of the cardiac harness and thus provide longitudinal structure to the harness. The connectors have a length oriented longitudinally relative to the rings so that adjacent rings are spaced apart a short distance.

As shown in FIG. 6, each of the rows 36 includes an undulating spring member 74. For purposes of this discussion, each undulating spring member includes a proximal portion 75 having a proximal apex 76 and a distal portion 78 having a distal apex 80. The connectors 52 connect adjacent rows by aligning the proximal apex of one row with the distal apex of an adjacent row, and a connector extends therebetween. The connectors define the spacing 82 between the distal apex of one row and the proximal apex of an adjacent row. The connector assembly illustrated in FIG. 6 illustrates an arrangement of connectors that is used as a pattern generally through all or a portion of one cardiac harness embodiment. In connection with this embodiment, and at least the embodiments discussed below in connection with FIGS. 6-9, the term "connector assembly" refers to at least the pattern and spacing of connectors between rows.

One way to describe the arrangement of connectors in a connector 52 in a connector assembly is by a transverse spacing T between connectors of adjacent rings or rows 36. The transverse spacing T is measured as the number of apices between a connector disposed on a proximal apex 76 of the row and the nearest connector that is disposed on the distal apex 80 of the row, when counting in a transverse direction (circumferentially). For example, in the embodiment illustrated in FIG. 6, the connectors have a transverse spacing T of 5. In other words, in the disclosed embodiment, there are three proximal apices and two distal apices, totaling five apices between the connectors. Of course, in other embodiments, the transverse spacing can be greater or less than 5. Further, the transverse spacing can vary through the harness. In the illustrated embodiment, however, the connector assembly is arranged such that there is a transverse spacing T of more than one apex between adjacent rows.

Figure 6A:
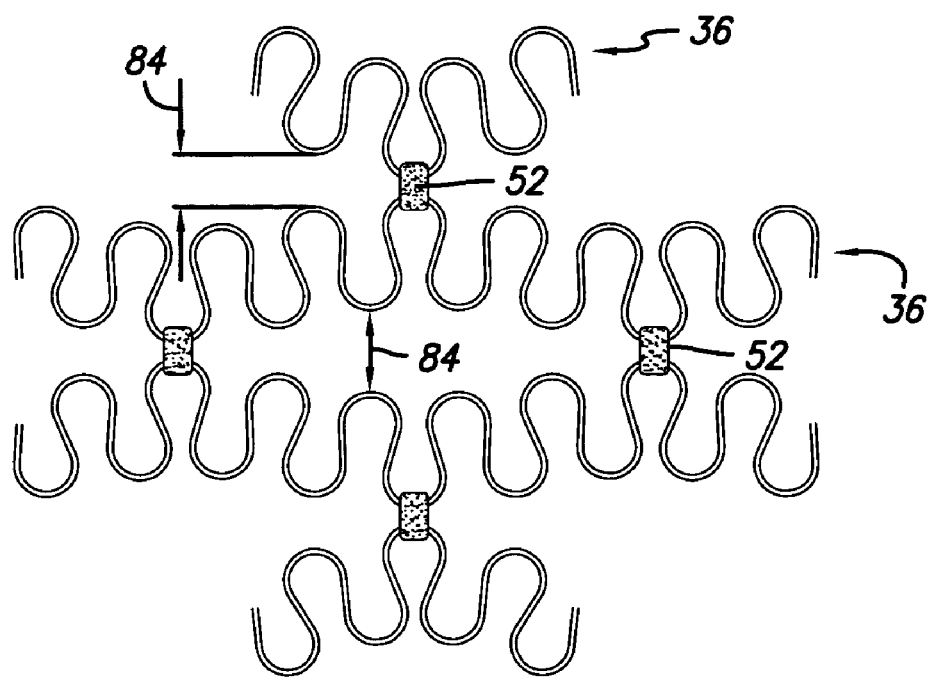
FIG. 6A depicts an enlarged partial plan view of a cardiac harness wherein the connectors form a pattern that permits distended spacing between adjacent rows.

With reference to FIG. 6A, it has been found that when a longitudinal force is applied to a harness 32 with a connector assembly having a transverse spacing T of more than one apex between adjacent rows 36, portions of the adjacent rows between the connectors 52 have a tendency to move longitudinally, while the distance between adjacent rows at the connector remains the same. As such, distended spaces 84 are formed between adjacent rows. As shown in FIG. 6A, the result of such distended spaces is that the rows of spring hinges 34 are somewhat deformed. In fact, the geometry of the undulating rows 46 can become significantly distorted and inconsistent. When mounting the cardiac harness onto the heart and during operation, the spring members are exposed to varying longitudinal and transverse stresses. Since the design of at least some embodiments of undulating rows are optimized for transverse stresses, distended spaces can result in inconsistent and irregular loading of the cardiac harness embodiment. This can reduce the efficacy of the harness and reduce the lifetime of the undulating rings.

Figure 7:
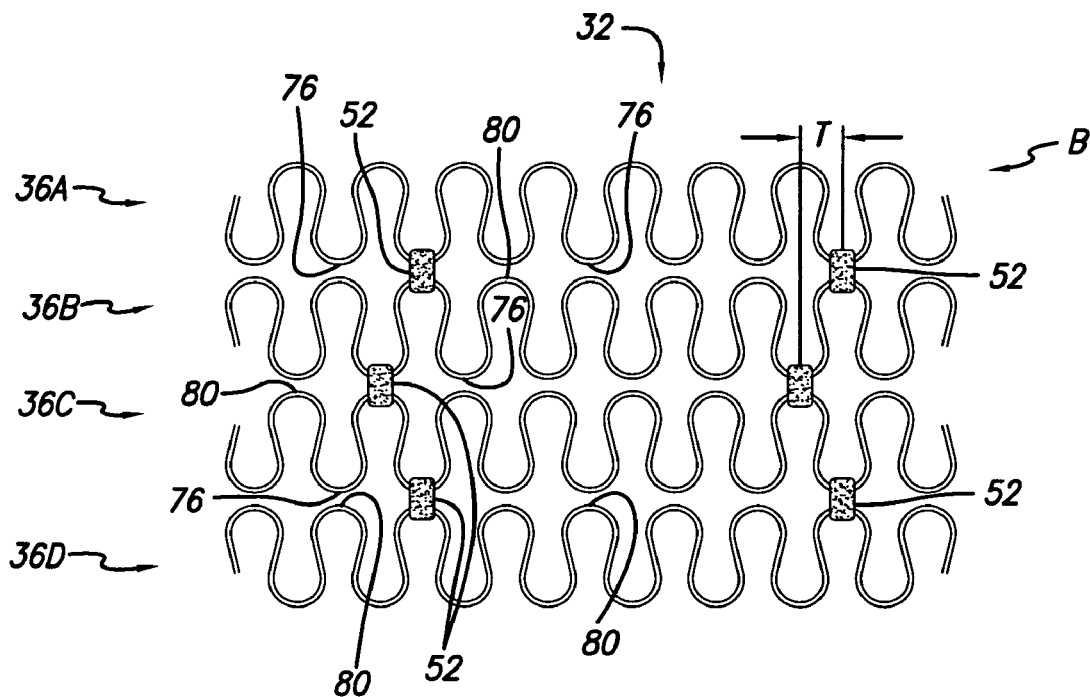
FIG. 7 depicts an enlarge partial plan view of a cardiac harness wherein the connectors form a connector assembly.

With reference to FIG. 7, a portion of another embodiment of a cardiac harness 32 is illustrated. The illustrated portion employs another embodiment of a connector assembly. In the illustrated embodiment, each connector 52 extends between a distal apex 80 of one row 36A and a proximal apex 76 of a spring member 34 on the adjacent row 36B. As shown in FIG. 7, a second row 36B is connected to a first row 36A by a connector 52 extending from a proximal apex of the first row connected to a distal apex of the second row. The second row is then connected to a third row 36C by a connector extending from a proximal apex of the second row to a distal apex of the third row. As shown, the connector between the second and third rows is arranged immediately adjacent the connector between the first and second rows so that the transverse spacing T between the connectors is only one apex. A similar disposition exists between the third row 36C and fourth row 36D and, preferably. through all or a portion of the harness. This arrangement is labeled and referred to as a "1-1-1" longitudinal structure. The transverse spacing T of the "1-1-1" longitudinal structure minimizes the number of spring member apices between adjacent connectors, and thus minimizes distended stretching of spring members between adjacent connectors. Thus, the longitudinal stretching of the cardiac harness when the harness is installed on the heart is substantially reduced.

In the embodiment illustrated in FIG. 7, two "1-1-1" connector assemblies (A, B) are shown. In one embodiment, several such connector assemblies extend from the apex 54 to the base 56 of the harness. It is to be understood that such connector assemblies can also extend only part way from the base to the apex. It is also to be understood that a cardiac harness may have two or more connector assemblies having different patterns of connectors.

Figure 8:
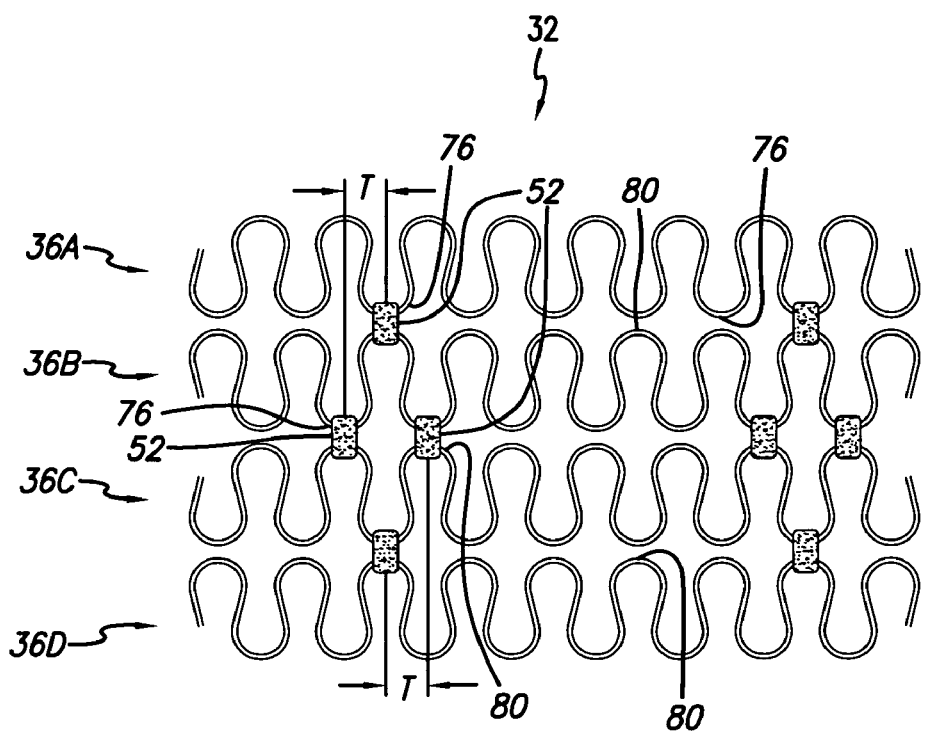
FIG. 8 depicts an enlarged partial plan view of a cardiac harness wherein the connectors form a connector assembly.

FIG. 8 illustrates a portion of another embodiment of a cardiac harness 32 connector assembly. In the illustrated embodiment, the connector assemblies are arranged in a "1-2-1" longitudinal structure. More specifically, the connector assemble is comprised of a single connector 52 interconnecting a proximal apex 76 of a first row 36A and a distal apex 80 of a second row 36B, followed by two connectors 52 connecting the adjacent proximal apices of the second row with two adjacent distal apices of a third row 36C, followed by a single connector interconnecting a proximal apex of the third row and a distal apex of a fourth row 36D. As shown in FIG. 8, the two connectors interconnecting the second and third rows are disposed on the apices immediately adjacent the apices supporting the single connector between each of the first and second and the third and fourth rows. The transverse spacing T between adjacent connectors of the rows in this connector assembly embodiment is one apex.

The illustrated arrangement lends further longitudinal rigidity to the cardiac harness, as longitudinal forces acting upon the harness are generally distributed through the connectors rather than the bending portions of the spring members. This is because there are no spring apices between connectors to allow the creation of distended spaces as illustrated in FIG. 6A. Additionally, the longitudinal stretching of the cardiac harness when the harness illustrated in FIG. 8 is installed on the heart is substantially reduced. Due to the longitudinal rigidity of the cardiac harness, it can be repositioned or moved on the heart by using forceps (or the physician's hand) to pull on the apex of the harness or to grasp and push on the base of the harness.

It is to be noted that although FIGS. 6-8 illustrate connector assemblies comprised of specific numbers of connectors 52, each connector assembly may advantageously be comprised of more than or less than the number of the connectors illustrated in FIGS. 6-8, depending on the particular harness 32 and/or utilization thereof contemplated. It is also to he understood that although just a few adjacent rows have been illustrated, the illustrated connector assembly arrangements are simply for illustration, and it is anticipated that such arrangements will extend longitudinally through all or at least a portion of the cardiac harness.

Figure 9:
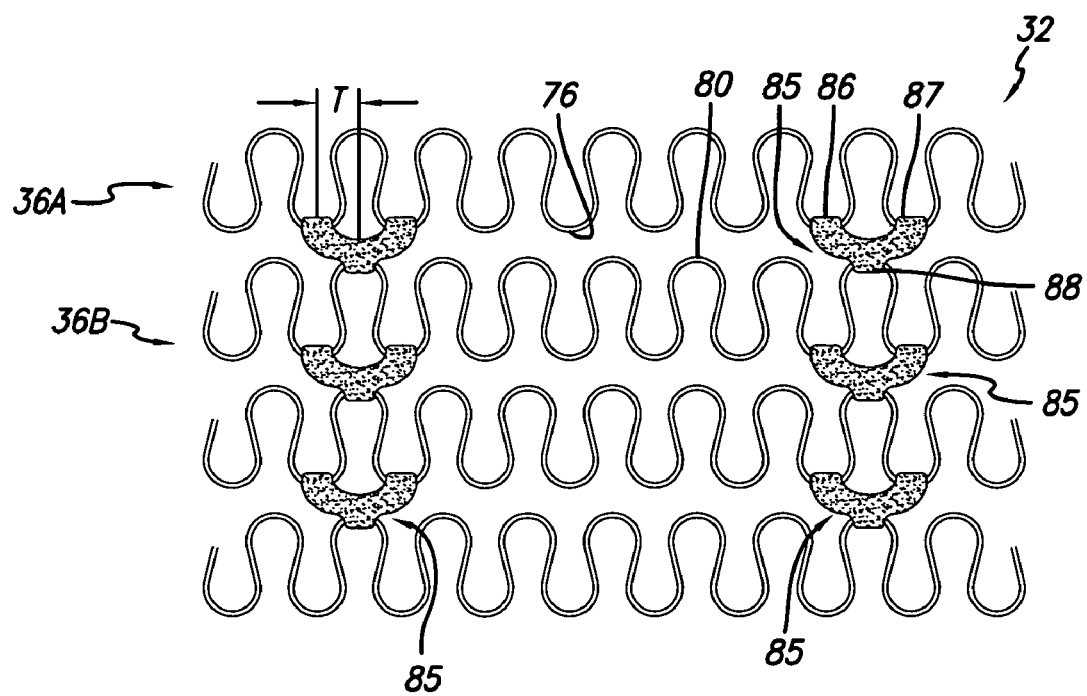
FIG. 9 depicts an enlarged partial plan view of a cardiac harness wherein Y-shaped connectors connect adjacent rows of the cardiac harness.

FIG. 9 illustrates another embodiment of a connector assembly for interconnecting rows of a cardiac harness. The connector assembly is formed of several Y-shaped connectors 85, each of which includes a first attachment portion 86, a second attachment portion 87, and a third attachment portion 88. The attachment portions give the connector a generally "Y-shaped" geometry. Preferably, the connector is formed of a semi-compliant material, such as silicone rubber or other similar material. In the embodiment illustrated in FIG. 9, the first and second attachment portions of each connector are attached to proximal apices 76 of a first row 36A, while the third attachment portion of each connector is attached to the distal apex 80 of an adjacent second row. In another embodiment, the proximal/distal arrangement is reversed.

As illustrated. the transverse spacing T between the first attachment portion 86 or second attachment portion 87 and the third attachment portion 88 is one apex. As such, when the harness is subjected to longitudinal forces, most or all of the longitudinal forces will be communicated through the Y-shaped connectors 85 and the bending portions of the undulating spring members 34 will encounter little or none of the longitudinal force.

It is to be understood that in other embodiments, the specific form and shape of a connector assembly may be different. Yet, the assembly may similarly be adapted to connect adjacent undulating rows so that a proximal portion of a first row is attached to a distal portion of an adjacent row in a manner that communicates longitudinal forces through the connectors and minimizes longitudinal distention of spring members due to such longitudinal forces.

Figure 10:
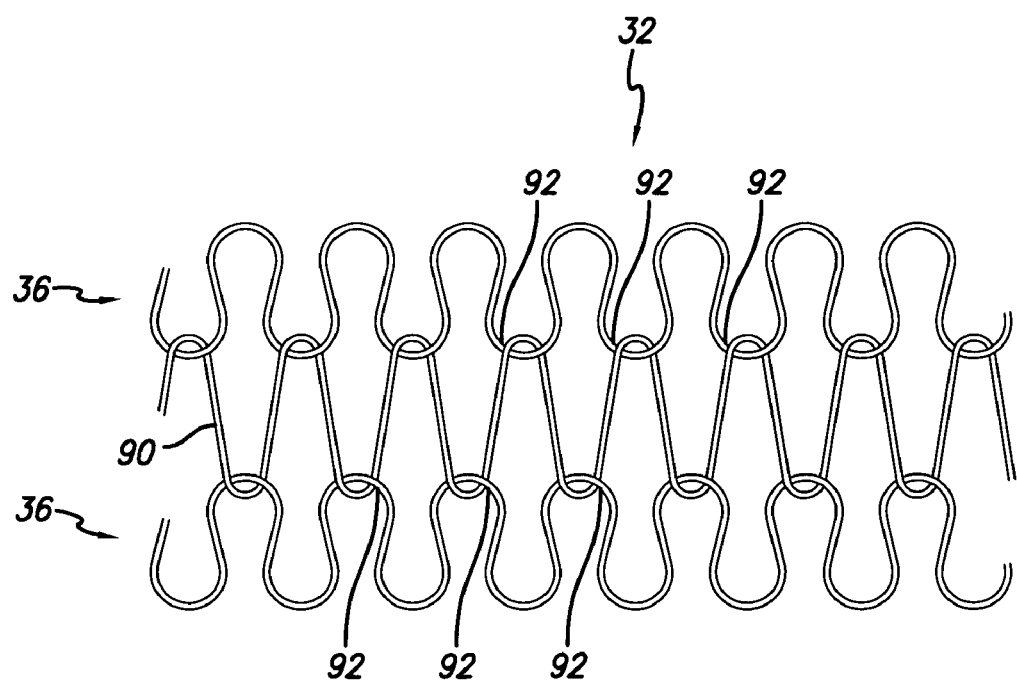
FIG. 10 depicts an enlarged partial plan view of a cardiac harness wherein a single elongated connector is woven between apices of adjacent rows.
Figure 11:
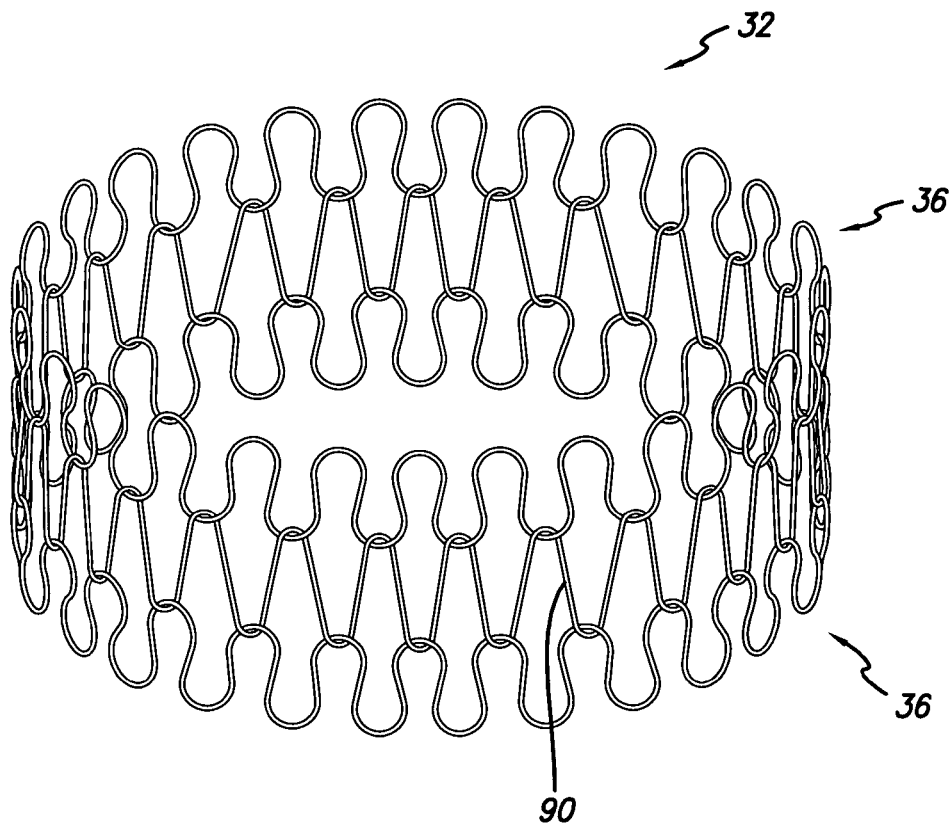
FIG. 11 depicts an enlarged partial plan view of a cardiac harness wherein a single connector is woven between all of the apices of adjacent rows.

FIG. 10 illustrates another embodiment of a connector assembly which is utilized for interconnecting rings of a cardiac harness. The connector assembly is comprised of a long, thin connector 90 which is interwoven between apices 92 (reference number 92 points to the apex region since the connector covers the apex) of adjacent undulating rows 36 of a cardiac harness 32. As shown in FIG. 11, the connector has a length sufficient to pass through every apex 92 of the adjacent rows and thus interconnects all of the undulations forming the adjacent rows. The connector preferably is formed of a semi-compliant dielectric material, such as silicone rubber or other similar material. In the embodiment illustrated in FIG. 11, the connector is formed from silicone tubing substantially similar to the silicone tubing discussed with reference to FIG. 3.

Figure 12:
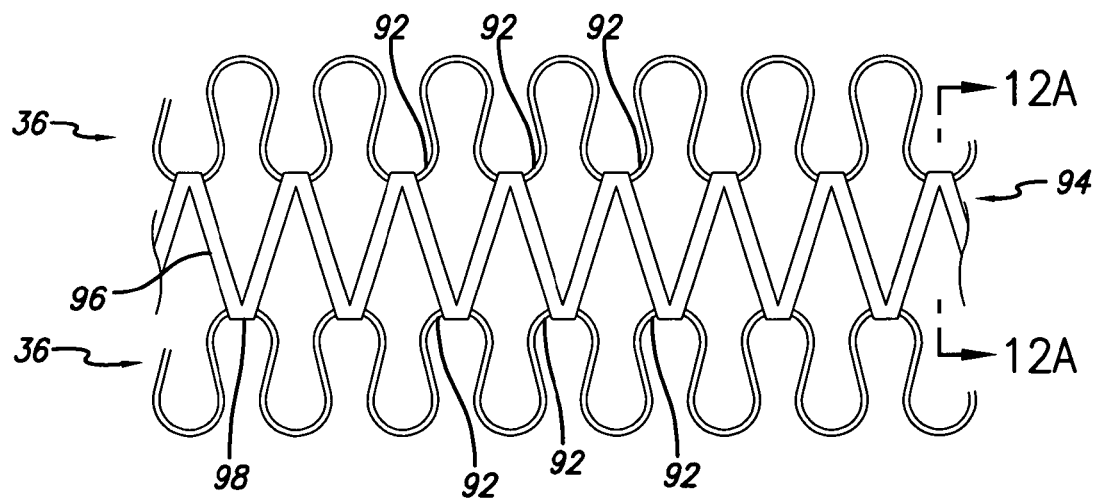
FIG. 12 depicts an enlarged partial plan view of a cardiac harness wherein a single connector is attached to the apices of adjacent rows.
Figure 12A:
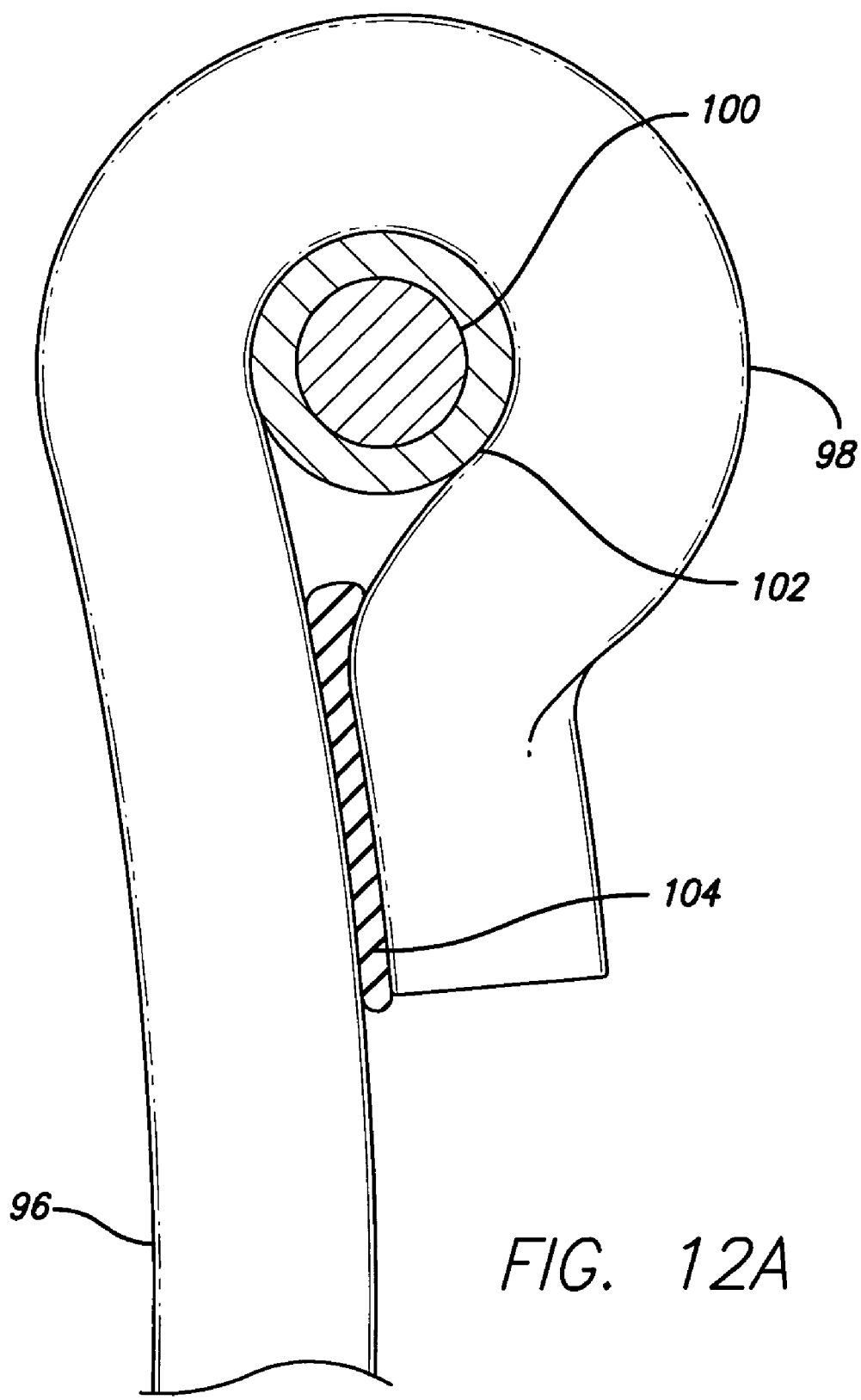
FIG. 12A depicts a cross-sectional view taken along lines 12A-12A showing attachment of the connector to an apex of one of the rows.

In another embodiment, illustrated in FIG. 12, a row connector is comprised of a long, thin strip 94 of dielectric material which is formed into numerous elongate portions 96 and attachment portions 98. The attachment portions are disposed at opposite ends of each elongate portion. The elongate portions interconnect all of the apices of adjacent undulating rows 36 of the harness. The attachment portions facilitate fastening the elongate portions of the apices 93. One embodiment of an attachment portion is illustrated in FIG. 12A, which is cross-sectional view of FIG. 12, taken along line 12A-12A. As shown, the attachment portion 98 is passed over the spring member apex 92 (apex region) and adhered to the underside of the elongate portion 96, thereby locking the spring member within the attachment portion. The wire 100 forming the cardiac harness has a dielectric coating 102, which is covered by the attachment portion in the area of the apex of the row. Preferably, an adhesive 104 is used to adhere the attachment portion to the elongate portion.

With continued reference to FIGS. 10 through 12A, because all of the apices participate in connecting the rows of the harness, distended spaces such as those shown in FIG. 6A are substantially eliminated. Additionally, the connectors shown in FIGS. 10 and 12 prevent the rows from becoming overturned, flipped over, or tangled with one another during installation of the harness on the heart.

It has been found that cardiac harnesses comprised of connector assemblies of the forms shown in FIGS. 10 and 12 exhibit low compliance in longitudinal tension, yet provide relatively high compliance in longitudinal compression. This facilitates normal longitudinal strain of the heart during the cardiac cycle. It has also been found that the connector assemblies of FIGS. 10 and 12 provide harnesses exhibiting relatively high compliance in shear. This allows adjacent rows to twist with respect to one another, and thereby allows for normal epicardial shear (i.e., torsion) during the cardiac cycle. Moreover, the connectors shown in FIGS. 10 and 12 generally uniformly distribute the compressive forces of the rows on the surface of the heart, thereby reducing the possibility that myocardial aneurysms may form between adjacent rows.

Figure 13A:
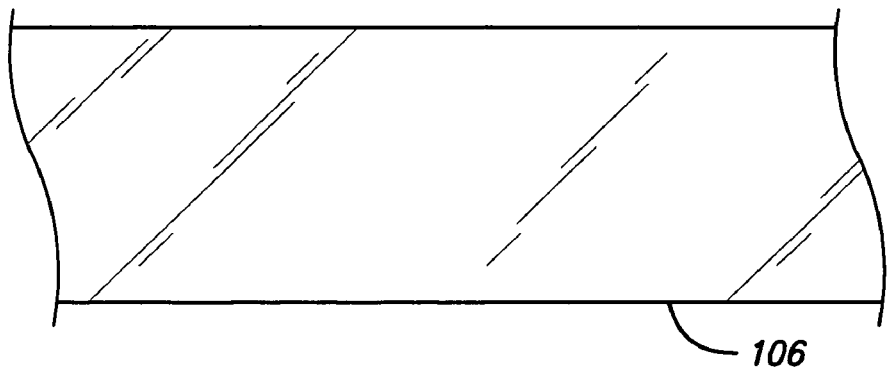
FIG. 13A depicts a plan view of a sheet of material used to form a connector.
Figure 13B:
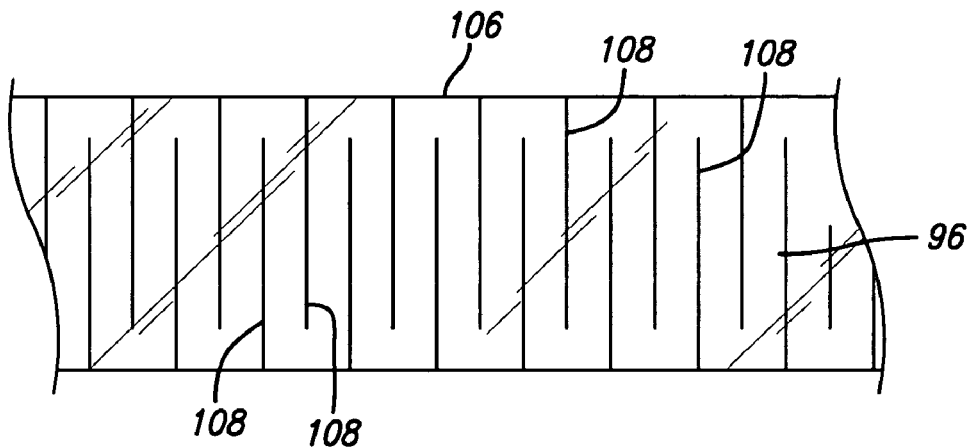
FIG. 13B depicts a plan view of a sheet of material having cuts that form an elongated connector.
Figure 13C:
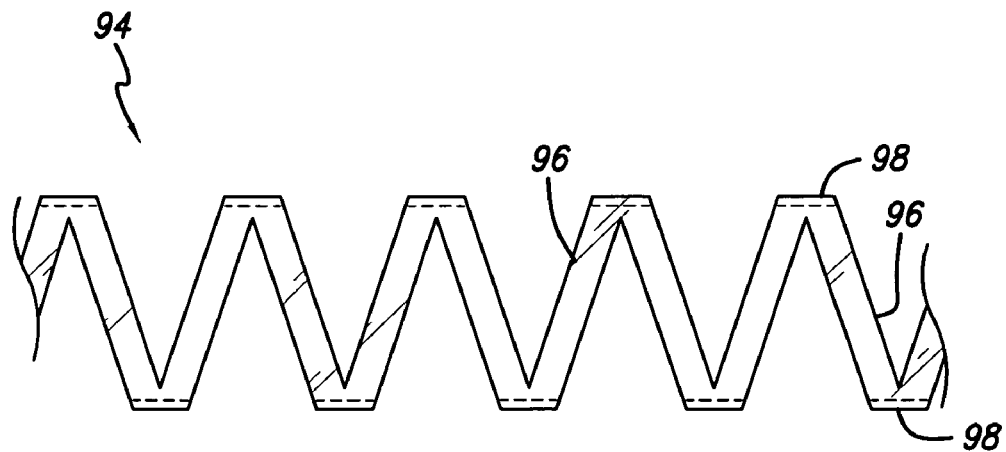
FIG. 13C depicts a plan view of an elongated connector.

With reference to FIGS. 13A through 13C, one embodiment of a method for making the connector 94 of FIG. 12 is shown. Initially, the connector is formed from a sheet 106 of material having properties and/or characteristics desired for the connector. Preferably, the sheet material is a dielectric, semi-compliant material such as silicone rubber or other similar material. As shown in FIG. 13A, the sheet has a length which is generally longer than its width. As shown in FIG. 13B, a series of cuts 108 are applied to the sheet on opposite sides. The cuts preferably are generally linear along a direction transverse to the length of the sheet. The cuts alternate from one side of the sheet to the other side to form a series of elongate portions 96 which are endwise attached to one another. An undulating connector 94 is thus provided upon stretching the sheet lengthwise, as shown in FIG. 13C.

In another embodiment, a row connector includes an elongate tube or wire formed of an elastomeric material such as silicone rubber wound between adjacent apices of adjacent undulating rows. In still another embodiment, the connecting member is not wound between every single adjacent apex. In still another embodiment, a connecting member is formed by molding a row connection member substantially in the shape of the cut connector shown in FIG. 13C.

Figure 14:
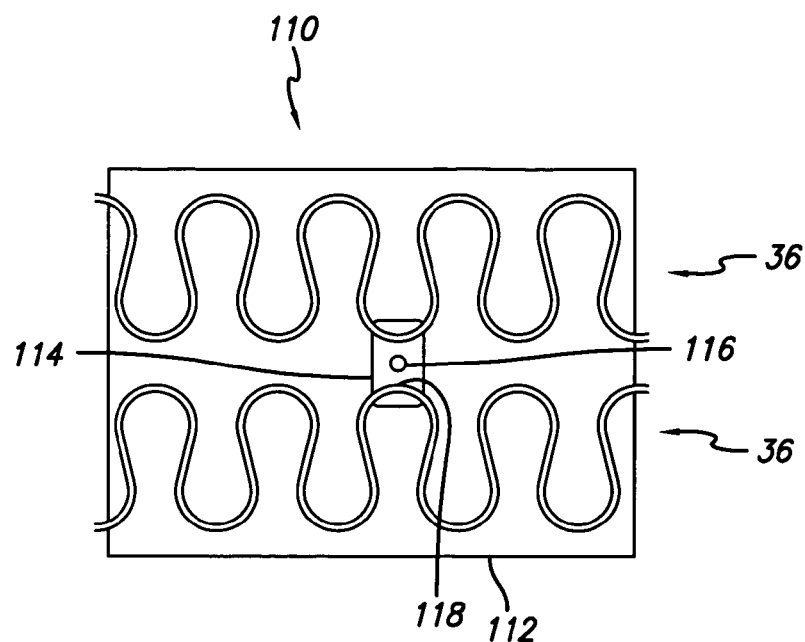
FIG. 14 depicts a plan view of a mold for forming connectors between adjacent rows of a cardiac harness.

With reference to FIG. 14, another example of a method and apparatus for interconnecting the elastic rows 36 of a harness 32 is provided. FIG. 14 discloses one embodiment of a mold 110 for making the connectors 52 shown and discussed in connection with FIG. 4, and for assembling a cardiac harness having adjacent undulating rows. The mold includes a base portion 112 and a connector portion 114. The connector portion includes a gate 116 for injecting a liquid material into the connector portion. The connector portion has a shape and size optimal for allowing the liquid material to solidify into a connector. Preferably, the liquid material used for the connectors is silicone rubber or other material suitable for making the connectors. The shape and size of the connectors can vary and the connectors can be formed with ridges or protrusions on the side facing the heart to increase frictional engagement between the connectors and the heart to hold secure the harness on the heart. The base portion is configured to receive at least two rows 36. The two rows are releaseably attached to the mold so that at least one apex 118 from each row passes within the connector portion. In one embodiment, the rows are fastened to the mold in a stretched state. This facilitates adjusting the positions of the rows on the mold. The mold preferably is made of Teflon or other similar material.

In operation, the connector portion 114 of the mold 110 is partially filled with liquid silicone rubber or another material selected for the connector 52. The liquid silicone rubber is injected into the connector portion through the gate 116. As discussed above, the two rows 36 are positioned on the mold so that one apex member 118 from each ring is positioned within the connector portion, as shown in FIG. 14. Once the apices are suitably positioned, the connector portion is filled to capacity with the liquid silicone rubber. The liquid silicone is then cured in the connector portion. In one embodiment, the liquid silicone rubber is baked in the connector portion at a temperature of about 150° C. for a period of about five minutes. The solidified connector is then removed from the mold along with the two rows.

In other embodiments, the connector portion 114 can have shapes and sizes different than those shown in FIG. 14, depending on the type of connectors desired. For example, in another embodiment, the connector portion may have a "Y-shape" as illustrated and discussed above in connection with FIG. 9. Moreover, the mold 110 may include several connector portions to facilitate assembling most or all of a harness.

Figure 15:
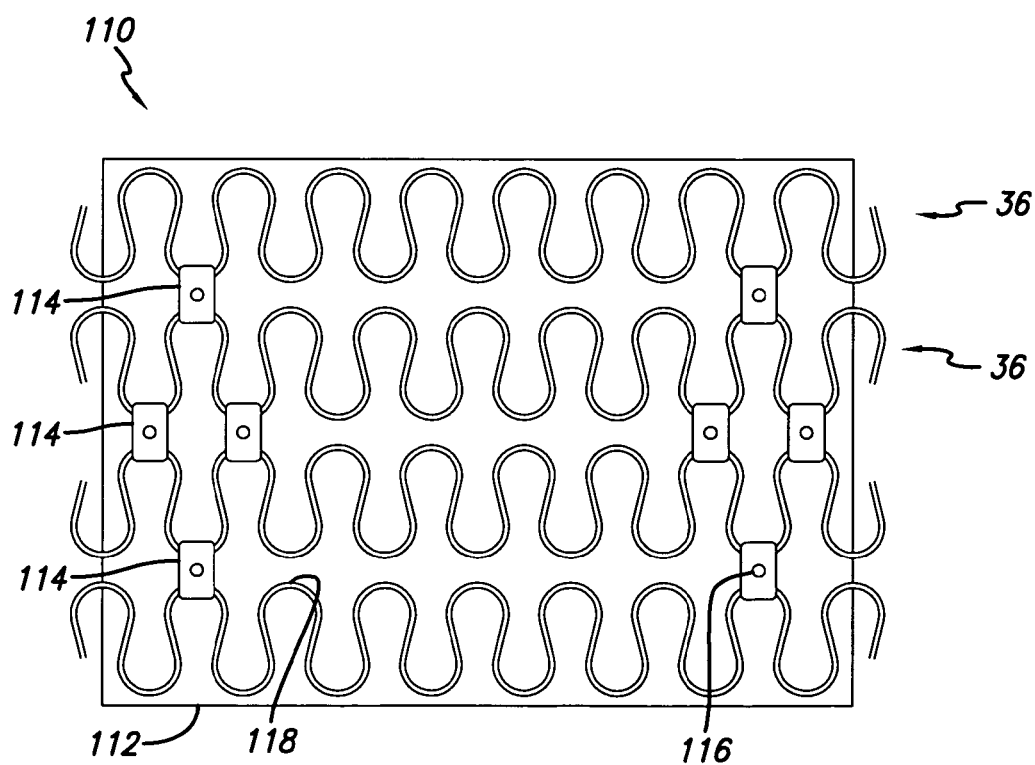
FIG. 15 depicts a plan view of a mold for forming connectors between adjacent rows of a cardiac harness.

FIG. 15 discloses one embodiment of a mold 110 for making a connector assembly comprising multiple connectors 52. The mold shown in FIG. 15 is configured for making connector assemblies of the form illustrated and discussed in connection with FIG. 8. Several rows 36 can be disposed in the mold shown in FIG. 15 and the multiple connector portions 114 can be filled with the liquid material simultaneously. It will be appreciated that in other embodiments, the positions of the connector portions on the mold may be changed to facilitate making other connector assemblies, such as any of the connector assemblies illustrated in FIGS. 6-9.

Molds of the type illustrated in FIG. 15 are particularly suitable for one method embodiment of making a cardiac harness 32, in which a totality of the elastic rows 36 (FIG. 3) comprising the harness are positioned in a mold 110 having multiple connector portions 114 positioned at locations suitable for forming connectors 52 between the elastic rows of the harness 32. The elastic rows are positioned in the mold in an arrangement which facilitates simultaneously forming all of the connectors between all of the elastic rows of the harness. Operation of the mold is substantially identical in all respects to the operation of the mold illustrated and discussed in connection with FIG. 14. Once the connectors are formed, the elastic rows are folded so that the opposite ends of each strand meet one another, thereby forming the rows of the harness. The opposite ends are secured to one another as illustrated and discussed in connection with FIGS. 5-5A.

Figure 16:
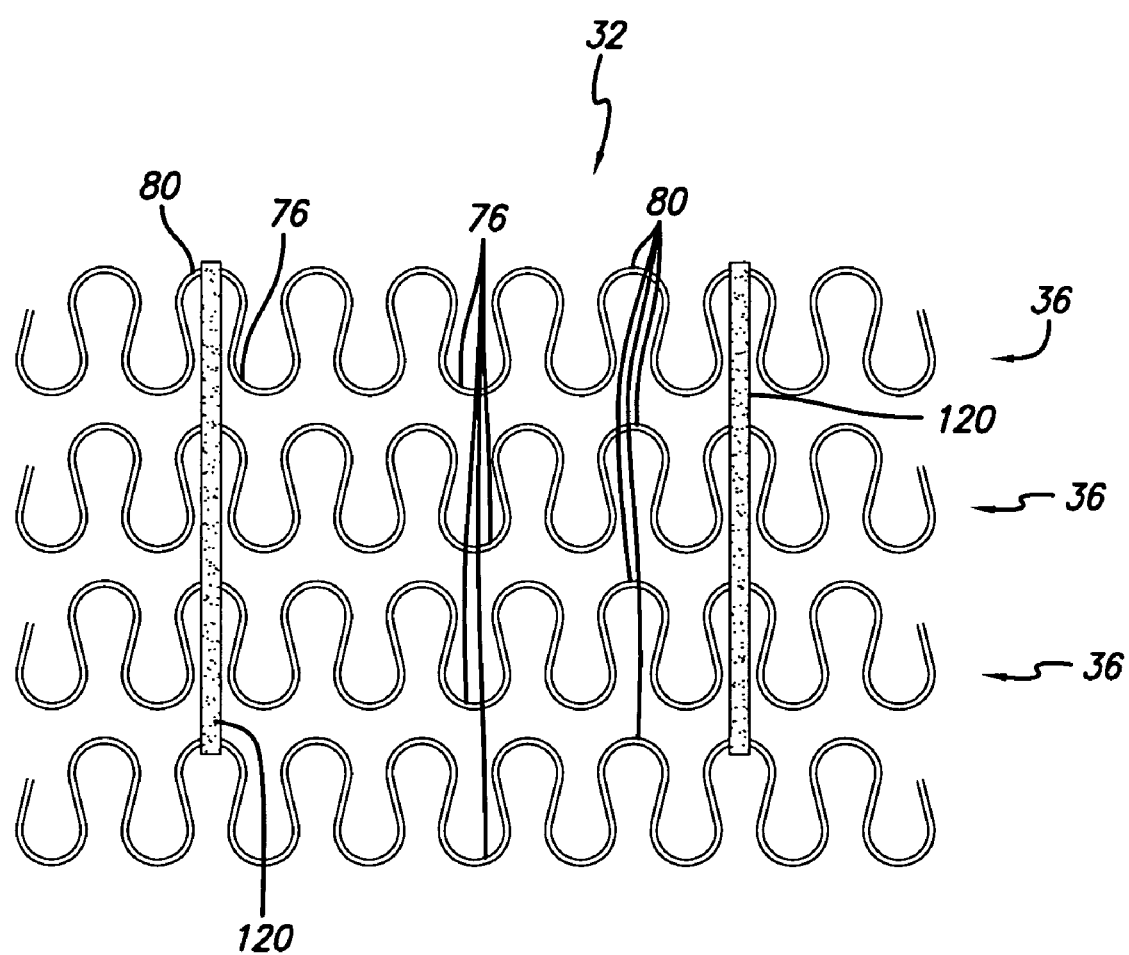
FIG. 16 depicts an enlarged partial plan view of a cardiac harness wherein connectors extend longitudinally along the rows of the cardiac harness attaching distal apices.

With reference to FIG. 16, a portion of another embodiment of a cardiac harness 32 is illustrated. The illustrated portion employs another embodiment of a connector assembly, in which a single elongate connector 120 spans several rows 36. More specifically, the elongate connector attaches to the distal apices 80 of several adjacent rows. In this embodiment, the spring elements 34 are in phase in that all of the distal apices 80 are in line. In a preferred embodiment, one elongate connector extends from a base portion 56 of the harness to an apex portion 54 of the harness. As such, longitudinal expansion of the harness at or near the connector is substantially entirely controlled by the connector. In another embodiment, an elongate connector spans three or more adjacent rows, and extends at least a portion of the distance between the apex and the base.

In the embodiment illustrated in FIG. 16, the elongate connectors 120 connect to the distal apices 80 of rows 36 spanned by the connector. It is to be understood that other arrangements may also be acceptable. For example, an elongate connector may connect only to proximal apices 76 of adjacent rows 36, or may connect to one or both of the proximal and distal apices 76,80 of adjacent rows.

Although this invention has been disclosed in the context of certain preferred embodiments and examples, it will be understood by those skilled in the art that the present invention extends beyond the specifically disclosed embodiment to other alternative embodiments an/or uses of the invention and obvious modifications and equivalents thereof. In addition, while a number of variations of the invention have been shown and described in detail, other modifications, which are within the scope of the invention, will be readily apparent to those of skill in the art based upon this disclosure. It is also contemplated that various combinations or subcombinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims.

We claim:

1. A cardiac harness for mounting on a heart, comprising: a plurality of undulating rows having a plurality of apices, each of the rows connected to an adjacent row by at least one connector; a plurality of the connectors arranged in a connector assembly, wherein a transverse spacing between connectors of adjacent rows within the connector assembly is no greater than one apex, and wherein the at least one connector connects to only one apex of a first row and more than one apex of a second row.

2. The cardiac harness of claim 1, wherein the at least one connector is generally Y-shaped.

3. The cardiac harness of claim 1, wherein at least some of the rows are arranged into 360° circumferential rows.

4. The cardiac harness of claim 1, further comprising a first connector assembly and a second connector assembly, the first connector assembly being arranged in a different pattern than the second connector assembly.

5. The cardiac harness of claim 1, wherein the rows have proximal apices and distal apices, the at least one connector between adjacent rows connects a proximal apex of a first row to a distal apex of a second row.

6. The cardiac harness of claim 1, wherein the connector is formed from an elastomer.

7. The cardiac harness of claim 1, wherein the connector is formed from silicone rubber.

8. The cardiac harness of claim 1, wherein longitudinal elasticity of the harness generally correlates to the elasticity of the connectors.

9. The cardiac harness of claim 1, wherein the connector member is formed from a flexible material.

10. The cardiac harness of claim 1, wherein the cardiac harness is configured for mounting on a beating heart.

* * * * *